US007005257B1

(12) United States Patent
Haas et al.

(10) Patent No.: US 7,005,257 B1
(45) Date of Patent: Feb. 28, 2006

(54) DETECTION OF ANTIBIOTIC RESISTANCE IN MICROORGANISMS

(75) Inventors: Rainer Haas, München (DE); Karlheinz Trebesius, Bad Endorf (DE); Heiko Apfel, Neusäss (DE)

(73) Assignee: SeaPro Theranostics International, Lelystad (NL)

( * ) Notice: Subject to any disclaimer, the term of this patent is extended or adjusted under 35 U.S.C. 154(b) by 0 days.

(21) Appl. No.: 09/673,645

(22) PCT Filed: May 21, 1999

(86) PCT No.: PCT/EP99/03527

§ 371 (c)(1),
(2), (4) Date: Oct. 31, 2000

(87) PCT Pub. No.: WO99/61660

PCT Pub. Date: Dec. 2, 1999

(30) Foreign Application Priority Data

May 22, 1998 (DE) ................................ 198 23 098
Apr. 13, 1999 (DE) ................................ 199 16 610

(51) Int. Cl.
*C12Q 1/68* (2006.01)
*C07H 21/02* (2006.01)
*C07H 21/04* (2006.01)

(52) U.S. Cl. ................... 435/6; 435/5; 435/29; 435/30; 435/32; 435/34; 536/23.1; 536/23.7; 536/24.32

(58) Field of Classification Search ............... 435/6, 435/91.2, 4, 29, 30, 32, 34; 536/23.1, 24.32, 536/24.33, 23.32, 23.33
See application file for complete search history.

(56) References Cited

U.S. PATENT DOCUMENTS

| 5,571,674 | A |   | 11/1996 | Hoshina et al. ................. 435/6 |
| 5,700,683 | A | * | 12/1997 | Stover et al. ........... 435/252.31 |
| 5,925,360 | A | * | 7/1999 | Meyers et al. ........... 424/220.1 |
| 6,228,575 | B1 | * | 5/2001 | Gingeras et al. ................ 435/5 |

FOREIGN PATENT DOCUMENTS

| WO | 93/22445 | 11/1993 |
| WO | 95/33074 | 12/1995 |
| WO | 95/34574 | 12/1995 |
| WO | 96/08582 | 3/1996 |
| WO | 98/20157 | 5/1998 |

OTHER PUBLICATIONS

Stratagene Catalog. 1988, p. 39.*
Versalovic et al. Antimicrobial Agents and Chemotherapy. Feb. 1996. 40: 477-480.*
Amann et al. Microbiological Reviews. Mar. 1995. 59: 143-169.*
Hiratsuka, NCBI Database, National Library of Medicine, National Institutes of Health (Bethesda, MD, USA), GenBank Accession Nol U27270, Jun. 1995.*
Versalovic et al., "Point mutations in the 23S rRA gene of *Helicobacter pylori* associated with different levels of clarithromycin resistance", Journal of Antimicrobial Chemotherapy, vol. 40, 1997, pp. 283-286.
Amann et al., "Fluorescent-oligonucleotide probing of whole cells for determinative, phylogenetic . . . ", Journal of Bacteriology, vol. 172, No. 2, 1990, pp. 762-770.
Morotomi et al., "Oligonucleotide Probe for Detection and Identifiation of *Campylobacter pylori*", Journal of Clinical Microbiology, vol. 27, No. 12, Dec. 1, 1989, pp. 2652-2655.
Ross et al., "Clinical resistance t erythromycin and clindamycin in cutaneous propionibacteria from acne patients . . . ", Antimicrobial Agents and Chemotherapy, vol. 41, No. 5, 1997, pp. 1162-1165.
Lucier et al., "Transition mutations in the 23S rRNA of erythromycin-resistant isolate sof *Mycoplasma pneumoniae*", Antimicrobial Agents and Chemotherapy, vol. 39, No. 12, 1995, pp. 2770-2773.
Meier et al., "Identification of mutations in 23S rRNA gene of clarithromycin-resistant *Mycobacterium intracellular*", Antimicrobial Agents and Chemotherapy, vol. 38, No. 2, 1994, pp. 381-384.
Sigmund et al., "Antibiotic resistance mutations in ribosomal RNA genes of *Escherichia coli*", Methods in Enzymology, vol. 164, 1988, pp. 673-690.
Cangelosi et al., "Detection of rifampin-and ciprofloxacin-resistant *Mycobacterium tuberculosis* . . . ", Antimicrobial Agents and Chemotherapy, vol. 40, No. 8, 1996, pp. 1790-1795.
Vester et al., "A plasmid-coded and site-directed mutation in *Escherichia coli* 23S RNA that confers resistance . . . ", BIOCHIMIE, vol. 69, 1987, pp. 891-900.
Pina et al., "Detection of point mutations associated with resistance of *Helicobacter pylori* . . . ", Journal of Clinical Microbiology, vol. 36, No. 11, 1998, pp. 3285-3290.
Van Doorn et al., "Rapid detection, by PCR and reverse hybridization, of mutations in the *Helicobacter pylori* . . . ", Antimicrobial Agents and Chemotherapy, vol. 43, No. 7, 1999, pp. 1779-1782.
Battles, Jane K., et al., Diagnostic Assay for *Heliobacter hepaticus* Based on Nucleotide Sequence of Its 16S rRNA Gene, J Clin Microbio vol. 33, No. 5, pp. 1344-1347 (1995).
Barrett, D.M., et al., "In Situ Hybridization for *Helicobacter pylori* in Gastric Mucosal Biopsy Specimens: Quantitative Evaluation of Test Performance in Comparison With the CLOtest and Thiazine Stain", J Clin Lab Anal 11:374-379 (1997).

* cited by examiner

*Primary Examiner*—Carla J. Myers
(74) *Attorney, Agent, or Firm*—Rothwell, Figg, Ernst & Manbeck, P.C.

(57) ABSTRACT

The invention relates to a process for detecting antibiotic resistances in microorganisms, in particular in bacteria, and to reagent kits which are suitable for implementing the process.

27 Claims, 1 Drawing Sheet

DETECTION OF ANTIBIOTIC RESISTANCE IN MICROORGANISMS

The invention relates to a process for detecting antibiotic resistance in microorganisms, in particular in bacteria, and to reagent kits which are suitable for implementing the process.

Zuckerkandel and Pauling (1965) who, in the article: "Molecules as documents of evolutionary history" were the first to point out the possibility of revealing the evolution of organisms by comparing the sequences of their appurtenant macromolecules, laid the foundation stone for developing an rRNA-directed in-situ hybridization for detecting pathogenic organisms. It was then Carl Woese who used this concept for working out the first natural classification system in prokaryotes (Woese, 1987). A further result of these investigations was that rRNA sequences exhibit so-called signature sequences which are typical of particular domains, phyla, families, genera and even individual species. Detecting these signature sequences with the aid of PCR primers or hybridization probes therefore makes it possible to identify bacteria on different taxonomic levels. In addition, the high number of rRNA molecules which are naturally present in the bacterial cell ($10^4$–$10^5$ in rapidly growing bacteria) increases the sensitivity of the method and made it possible to use in-situ hybridization techniques which employ rRNA as the target molecule. Using radioactively labeled oligonucleotide probes, Giovannoni et al. 1988 were the first to be able to detect rRNA in whole bacterial cells and, one year later, DeLong et al. (1989) carried out such an in-situ hybridization using fluorescence-labeled oligonucleotides.

Recently, this technique has been employed frequently, particularly in environmental microbiology. The location of particular physiological groups (Wagner et al., 1993; Ramsing et al., 1993) and the influence of particular agents on the composition of the population of an ecosystem (Wagner et al., 1995) were the focus of interest in this connection.

However, this technique has also been employed successfully for detecting bacteria in the food hygiene sphere (Beimfohr et al., 1993). Medical microbiology is another field of microbiology in which rRNA-directed whole-cell hybridization is applied.

Thus, *H. influenzae* has been detected in throat swabs taken from children (Forsgren et al., 1994), *Candida* species have been detected in blood cultures and tissue samples taken from artificially infected animals (Lischewski et al., 1996, Lischewski et al., 1997), pathogenic *Yersinia* species have been detected in tissue sections, stools and throat swab samples (Trebesius et al., 1998), and *salmonella* have been hybridized as successfully in swabs (Nordentoftet al., 1997) as have bifidobacteria in stool samples (Langendijk et al., 1995).

As various investigations have demonstrated, the number of ribosomes in rapidly growing, heterotrophic bacteria depends heavily on the growth rate and the physiological activity of the organism (Schaechter et al., 1958). Since the quantity of bound probe is proportional to the quantity of rRNA, the state of growth of a cell can also be determined indirectly by way of the hybridization-mediated fluorescence (DeLong et al., 1989).

A comparison of the translation apparatus in eukaryotic cells and in bacterial cells shows considerable differences in the function and structure of the individual components. These differences create a therapeutic window for a series of active compounds which intervene specifically in the bacterial translation process but which do not intervene in the eukaryotic translation process. Table 1 lists frequently employed antibiotics which intervene in the translation process in the bacterial cell. These active compounds possess the second highest worldwide market share, coming after the antibiotics which are directed against peptidoglycans.

However, the massive therapeutic employment of these substances leads to the emergence of resistances in clinical isolates and consequently to therapy failures.

A number of causes may be responsible for the appearance of such a mutation:
(1) Change in the target site for the antibiotic
(2) Modification of the antibiotic
(3) Change in the transport of the antibiotic In the case of the MLS antibiotics (macrolide, lincosamide, streptogramin B), which achieve their effect by blockading the ribosomal peptidyltransferase center, investigations carried out on clinical isolates lead to the conclusion that changes in the target site for the antibiotic are responsible for the development of resistance in the overwhelming majority of cases (Versalovic et al., 1997). Several variants are also conceivable in this connection.
(1) Mutation of ribosomal proteins
(2) Mutation of the rRNA
(3) Posttranscriptional modification Whereas it was generally assumed previously that change in ribosomal proteins was mainly responsible for the development of resistance, experimental data of more recent origin militate against such a theory and instead support the thesis that changes which take place directly on the ribosomal RNA (posttranscriptional methylation or mutation) lead to the development of resistance.

TABLE 1

| Class/Active compound | Use |
|---|---|
| Aminoglycoside/aminocyclitol antibiotics | Market share: 3% |
| (Dihyro) streptomycin | Tuberculosis therapy; resistance frequent |
| neomycin, paromomycin | oral and topical use |
| kanamycin | parenteral administration; resistance frequent |
| gentamicin, tobramycin, amikacin, netilmicin, sisomicin | new; broad spectrum (not Streptococci or Enterococci; ototoxic and nephrotoxic; blood level control) |
| spectinomycin | penicillinase-resistant gonococci |
| Lincosamides | |
| Lincomycin, clindamycin | Gram-positive bacteria and Gram-negative anaerobes; good penetration into bone tissue; in the case of toxin formers |
| Macrolides | Market share: 11% |
| Erythromycin, roxithromycin, clarithromycin, Azithromycin | Against Gram-positive and Gram-negative cocci, chlamydias and mycoplasmas, Helicobacter; good ability to traverse the membrane → intracellular bacteria |
| Tetracyclines | Market share: 3.5% |
| Tetracycline, oxytetracycline, rolitetracycline, doxycycline, minocycline | Broad spectrum, including chlamydias and rickettsias; predominantly bacteriostatic; resistance frequent; deposition on teeth in infants; |

Thus, carbomycin was able to inhibit the in-vitro peptidyltransferase activity which was exhibited by protein-free 23S rRNA extracts (Noller et al., 1992). Furthermore, the affinity constants for the binding between erythromycin and ribosomal proteins, such as L15, which are claimed to be potential candidates for the appearance of resistance, are several orders of size less than those which were ascertained for complete ribosomes (Weisblum, 1995). In particular, however, the lack of erythromycin-resistant clinical isolates which have a mutation in their ribosomal proteins indicates that this mechanism of resistance is more likely to be of little importance (Weisblum, 1995).

However, the other two mechanisms of resistance are frequently encountered, with a striking observation being that the target region for both changes relate [sic] to particular bases in domain V of the 23S rRNA (Brimacombe, 1990).

An adenine residue in *E. coli* position 2058 (numbering according to Brosius et al., 1981), which residue is located in the tertiary structure of the 23S rRNA between helices 73 and 74 (numbering according to Brimacombe et al., 1980), is the substrate for the modification by methylases of the erm family which have been isolated from various macrolide-resistant clinical isolates (Weisblum, 1995). An A→G transition in this position also leads to a resistance phenotype in a number of phylogenetically dissimilar bacteria (*Mycobacterium intracellulare* (Meier et al., 1994), *H. pylori* (Versalovic et al., 1997), *E. coli* (Sigmund et al., 1988, Vester and Garrett, 1987), *Propionibacterium acnes* (Ross et al., 1997) and *Mycoplasma pneumoniae* (Lucier et al. 1995). Table 2 lists a number of other mutations in the peptidyltransferase center of the 23S rRNA which are found in resistant bacteria. The conserved nature of the positions which lead to MLS resistance, and their discovery in a very wide variety of phylogenetic groups (not only bacteria), demonstrates the general nature of this phenomenon. Since the discovery of these mutations is relatively recent, it is to be expected that modifications/mutations of the rRNA/rDNA will be positively identified in the coming years as being the cause of resistance development in a number of other clinical isolates. Experimental evidence pointing to this already exists in the case of the Mollicutes (*Mycoplasma* and *Ureaplasma*) (Palu et al., 1989, Stopler and Branski, 1986), for which MLS antibiotics are also the therapeutic agents of choice.

TABLE 2

| Mutation | Species | Phenotype |
| --- | --- | --- |
| G2057A | P. acnes | $Cla^R$, $Ery^R$ |
| A2058G | P. acnes | $Cla^R$, $Ery^R$ |
| A2059G | P. acnes | $Cla^R$, $Ery^R$ |
| A2058G | M. pneumoniae | $Ery^R$ |
| A2059G | M. pneumoniae | $Ery^R$ |
| C2611U | E. coli | $Ery^R Lin^R Sgb^R$ |
| G2032A | E. coli | $Ery^{HS} Cln^R Cam^R$ |
| G2032U | E. coli | $Ery^{HS} Cln^S Cam^S$ |
| G2032C | E. coli | $Ery^{HS} Cln^S Cam^S$ |
| G2057A | E. coli | $Ery^R$, $Cam^R$ |
| A2058G | E. coli | $Ery^R$ |
| A2058U | E. coli | $Ery^R$ |
| A2058G | M. intracellulare | $Cla^R$ |
| A2053C | M. intracellulare | $Cla^R$ |
| A2058U | M. intracellulare | $Cla^R$ |
| A2053G | H. pylori | $Cla^R$ |
| A2053C | H. pylori | $Cla^R$ |
| A2059G | H. pylori | $Cla^R$ |
| A2503C | E. coli | $Cam^R$ |

Table modified in accordance with the Weisblum, 1995, reference. Cam, chloramphenicol, Cla, clarithromycin, Cln, clindamycin, Ery, erythromycin, Lin, lincomycin, Sgb, streptogramin type B. HS, hypersensitive; R, resistant; S, sensitive.

In view of the increasing number of antibiotic resistances in clinically relevant bacteria, the rapid identification of resistant bacteria is assuming ever greater importance. The number of pathogenic bacterial species which are resistant to at least one therapeutically important antibiotic is continually increasing. In view of this situation, it is only possible to implement an effective therapy when the resistance status of the pathogenic organism is known. The methods for determining the resistance status of bacteria which are generally practised are essentially based on time-consuming growth tests which investigate the efficacy of the antibiotics which can be employed therapeutically. To this end, the bacteria have, as a rule, to be cultured twice, a procedure which lasts approx. 48 hours. The investigation of slowly growing organisms lasts correspondingly longer. According to the current state of the art, therefore, a highly effective therapy can only be initiated after a time delay of at least 1 to 2 days.

One approach to solving the problem of rapidly identifying antibiotic resistances in bacteria, in particular in the case of those antibiotics which are directed against the translation apparatus of the microorganisms, is that of improving the method of in-situ hybridization for detecting point mutations. The components of the translation apparatus are present in a large number of copies in a cell and can consequently be investigated directly, i.e. without any additional amplification step. The rRNA, which, according to more recent findings, is intimately involved in expressing antibiotic resistances and can consequently be employed as an indicator, is of particular interest in this connection.

In the remarks which follow, the procedure for developing probes for determining antibiotic resistance is described using the clinically important bacterium *Helicobacter pylori* as an example, while the essential components of appropriate test kits are also indicated by means of examples. An appropriate test for determining resistance can then be derived for each clinically relevant bacterium and each therapeutically relevant antibiotic using these guidelines.

The development of antibiotic resistances as a result of mutations in ribosomal nucleic acid sequences also has consequences for treating *Helicobacter pylori* infections. While the occurrence of spiral bacteria in the mucous membrane of the human stomach has been reported since the beginning of this century (Bizzozero, 1893), the fact that the organisms were pathogenic was only realized, and scientifically acknowledged, when Marshall and Warren (Warren and Marshall, 1983; Marshall et al., 1984) successfully isolated and cultured this bacterium from the mucous membrane of the stomach of a patient suffering from a gastric ulcer (ulcus ventriculi). As the first analyses showed, the isolated microorganisms were Gram-negative, spiral bacteria which were extremely mobile and possessed the unusual ability to survive in strongly acid medium (up to approx. pH 1). Originally designated *Campylobacter pylori*, the organisms were finally grouped, on the basis of their biochemical and morphological properties, in the newly established genus "*Helicobacter*" (Goodwin et al., 1989).

In 1987, Dent and coworkers were the first to identify a corkscrew-like organism in the mucous membrane of the human stomach and to designate it "*Gastrospirillum hominis*". Since such a bacterium has so far only been successfully cultured in exceptional cases, assignment to this "species" is made on the basis of location in the mucous membrane of the human antrum and of cell morphology (rod which is wound in a corkscrew-like manner). In 1993, Solnick and coworkers determined the 16S rRNA sequence of two "*Gastrospirillum hominis*" rods and established that this bacterium had to be assigned to the genus "*Helicobacter*". They consequently proposed the name "*Helico-* bacter heilmannii". It already became clear in this investigation that it did not in fact appear justified to bring these two strains together under the umbrella of one species since the difference in the 16S rRNA sequence was more than 3.5% (it is arte legis to regard two isolates as being different species from 3% onwards), whereas the difference between one of the strains (Gh2) and *Helicobacter felis* was only 1.5%. A *H. heilmannii* which it was possible to culture was described by Holck et al. 1997. However, sequencing data showed that this organism is more closely related to the newly described *Helicobacter salomonis* than it is to the *H. heilmannii* described by Solnick.

"*Helicobacter heilmanii*" (formerly "*Gastrospirillum hominis*") is therefore a phylogenetically heterogeneous group of *Helicobacter* species which are rarely found in the mucous membrane of the human stomach but which are, precisely like *H. pylori*, causatively involved, inter alia, in the development of gastric ulcers (Yeomans et al., 1996). Assignment to this group is made on the basis of morphological criteria (large rods which are wound in a corkscrew-like manner).

The importance of *Helicobacter* infection, and the consequence of this discovery, became clear within a few years. Epidemiological investigations carried out by Taylor and Blaser (1991) showed that *Helicobacter* infection occurs worldwide and that approx. 50% of the population are infected with these bacteria, with the infection rate being higher in developing countries than in industrialized countries. Another observation is that the probability of a chronic infection with *Helicobacter* increases drastically with increasing age. As a consequence, *Helicobacter* infections are among the most frequently occurring chronic bacterial infections in humans.

It is nowadays known that infection in humans inevitably leads to the triggering of a bacterial gastritis (type B gastritis). It is furthermore accepted as having been proved that *Helicobacter* infections also play a causative role in the development of gastric and duodenal ulcers (ulcus ventriculi and ulcus duodeni) (Hentschel et al., 1991).

According to a study carried out by Forman et al. (Forman et al., 1993), an *H. pylori* infection leads to a 6 to 12-fold increase in the risk of developing some forms of gastric carcinoma (adenocarcinoma). The more rarely occurring MALT (mucosa associated lymphoid tissue) lymphomas of the stomach, which are regarded as being the precursors of B cell tumors of the immune system, are also suspected of being a consequence of infection with *Helicobacter*. In this regard, it has been demonstrated that *Helicobacter heilmannii* has a greater potential for causing cancer than does *Helicobacter pylori* and is causatively responsible for gastric MALT lymphoma (Stolte et al., 1997; Regimbeau et al., 1998). Providing appropriate patients with antibacterial treatment, involving the successful eradication (total elimination) of *Helicobacter*, leads to both gastric ulcers and low-grade MALT lymphomas being healed (Sipponen and Hyvärinen, 1993; Isaacson and Spencer, 1993; Stolte and Eidt, 1993).

Before the existence of *Helicobacter* spec., and their importance for ulcer diseases, was known, these diseases were treated with antacids or $H_2$ receptor antagonists. The latter are substances which inhibit the secretion of acid by the parietal cells of the stomach. The effect of these drugs is usually to cause the ulcers to heal; since, however, the drugs do not eliminate one of the causes of these ulcers, namely the infection with *Helicobacter*, the ulceration recurs (recidivation) after a short period of time in most cases.

Another therapy which is frequently employed in association with ulcerations is that of bismuth treatment. Various bismuth salts (CBS, BSS) have a bactericidal effect on *Helicobacter*. However, total eradication of the organism is only achieved in 8–32% of cases. While the treatment apparently leads to a transient suppression of the organism, the infection flares up again in most cases after the treatment has been discontinued. A more long-lasting therapy with high doses leads to an accumulation of the substance in the liver and kidneys and in the nervous system and has considerable neurological side effects (Malfertheiner, 1994).

Since it was realized that the gastroduodenal ulcer diseases were infectious diseases, an aim of the treatment has been that of eradicating the pathogens with antibiotics. However, monotherapy with various antibiotics (amoxycillin, tetracycline, nitrofuran, furazolidine, and erythromycin, inter alia) turned out to be unsatisfactory since, with these drugs too, the organisms are only eradicated in 0–15% of the treatments. The previously recommended dual therapies using an acid blocker and an antibiotic also resulted in a high proportion of failures (Malfertheiner, 1994).

At present, the most successful treatment is achieved by the combination of an acid blocker (e.g. omeprazole) and two antibiotics in the form of the "French" triple therapy (amoxicillin and clarithromycin) or, in the case of allergy to penicillin, the "Italian" triple therapy (clarithromycin and metronidazole), which triple therapies can lead to eradication rates of 80–95%. Because of its favorable properties, clarithromycin is increasingly becoming the agent of choice (Graham, 1995). A four-fold therapy (Proton pump inhibitor, bismuth salt, tetracycline and metronidazole or clarithromycin) is recommended in the case of therapeutic failure due to the bacteria being resistant to clarithromycin or metronidazole, respectively. While this scheme promises success rates of about 95%, it nevertheless also suffers from substantial side effects.

The antibiotic resistance status of the bacteria is an important prerequisite for the success of the therapy.

The failure rate of the treatment increases markedly as soon as there is resistance to only one of the two antibiotics employed (Buckley et al., 1997). The observation that the number of metronidazole-resistant and clarithromycin-resistant *H. pylori* isolates has been steadily increasing recently certainly gives cause for disquiet. While the reason for this is not known, it could lie in the increasing number of therapies for eradicating *H. pylori*, in particular the dual therapies using one antibiotic which have frequently been implemented in the recent past and in which resistances frequently appear. A resistance to macrolide antibiotics such as clarithromycin or erythromycin is due to a point mutation in a particular region of the 23S rRNA. Such mutations apparently occur spontaneously and can readily be isolated by appropriate selection with an antibiotic. Rapid and reliable determination of the resistance status of *Helicobacter* isolates prior to therapy is therefore of great importance for the future.

The simplest method of detecting an acute *Helicobacter* infection with relative certainty is the so-called breath test (Desroches et al., 1997). This test measures the decomposition of orally administered, $^{13}C/^{14}C$-labeled urea into $^{13}CO_2$ or $^{14}CO_2$ and $NH_4$ by the bacterial urease. The $^{13}CO_2$ or $^{14}CO_2$ reaches the lungs via the blood circulation and is released in the lungs by way of the natural gas exchange and consequently becomes measurable in the respiratory air. The respiratory air is analyzed in a special appliance which is only possessed by special laboratories, so that the results are often obtained at a different site from that at which the samples were taken and there is consequently a delay in receiving them. Other noninvasive methods are based on PCR reactions which are carried out using stool or saliva samples (Schwarz et al., 1997). While these methods possess a very high degree of sensitivity, experience indicates that false-positive results occur very frequently in routine operation. Furthermore, these methods require a basic provision of apparatus and molecular biologicals which are not available in a general medical practice. This means that, in this case too, the samples have to be sent to special laboratories which means in turn that there is no possibility of obtaining the results rapidly. Indirect methods, which detect anti-*Helicobacter* antibodies in the serum or saliva, in turn suffer from the disadvantage that it is not possible to detect an acute infection beyond doubt.

As a rule, a gastroscopy is carried out when a positive breath test result has been obtained. A gastroscopy is often carried out in the case of a negative result as well, in particular when the symptoms do not subside after conventional therapy with proton blockers. As a rule, tissue samples are removed during a gastroscopy, in particular when it is possible to identify marked changes such as inflammations or ulcers. These tissue samples are examined histologically for benign or malignant tissue changes. Microbiological investigations, which are intended to assign the organism unambiguously and to determine its minimum inhibitory concentration (MIC) value, are carried out, in particular. These results make it possible to plan a specific therapy and consequently guarantee a high degree of success. In order to perform the microbiological investigations, it is necessary to culture the organism, a procedure which can take several days. After that, an MIC value determination is carried out, with this determination likewise being time-consuming and making it necessary to culture the organism. This investigation delays the beginning of the therapy substantially such that many doctors dispense with this investigation, which is to the disadvantage of the patient. The consequence of this is that doses of antibiotic which are too high, and which are accompanied by massive side effects, are employed in a therapy. On the other hand, the dose of antibiotic employed can be too low because no detection of antibiotic-resistant organisms was carried out. A rapid and reliable identification of the organism which is possibly causing the disease, and the immediate determination of its resistant status, are therefore of the utmost importance.

Coccoid forms of *H. pylori* have been described in the literature on a number of occasions. However, the clinical importance of these stages is the subject of controversy. Some authors postulate that coccoid forms are a morphological manifestation of cell death and can no longer revert to the vegetative form (Kusters et al., 1997). Other groups assume that these bacteria are viable but non-culturable VNC). Infection experiments carried out on various animal models have not been able to unambiguously clarify the question of whether it is possible to activate the coccoid form so as to convert it into the vegetative form. Eaton and coworkers successfully infected minipigs with vegetative *H. pylori*, whereas coccoid forms did not give rise to any infection in this model (Eaton et al., 1995). By contrast, two independent research groups have reported successful infection with VNC *H. pylori* in the mouse model (Cellini et al., 1994; Wang et al., 1997).

Using stomach tissue sections obtained from biopsy material, Chan et al. successfully detected coccoid forms directly in the human stomach. The authors were able to detect coccoid forms of *H. pylori* in 82.8% (53/64) of the biopsy samples examined using a hematoxylin-eosin stain (Chan et al., 1994). Cao et al. used a monoclonal antibody for specifically detecting coccoid *H. pylori* in the tissue section. In this case too, coccoid forms of *H. pylori* were detected, in addition to the vegetative forms, in 100% of the antrum biopsies (9/9) (Cao et al. 1997).

Other studies show that coccoid forms can be preferentially induced by $O_2$ stress and by administering antibiotics (bismuth subcitrate, erythromycin, amoxicillin and metronidazole) (Donelli et al., 1998; Bode et al., 1993; Sorberg et al., 1996; Berry et al., 1995), with polyphosphates evidently being used as an energy depot which could be sufficient for at least 3 months (Bode et al., 1993). Binding to epithelial cells and the ability to carry out signal transduction (IL-8 induction, rearrangement of the cytoskeleton, binding of plasminogen, lactoferrin and vitronectin on the bacterial surface) appear to be retained in the coccoid form at a level comparable to that in the vegetative forms (Khin et al., 1996; Segal et al., 1996). It appears likely that the coccoid form is a survival form of *Helicobacter*.

The invention relates to a novel process for determining, in microorganisms, in particular in bacteria, antibiotic reagents [sic] which are based on altered nucleic acid sequences, in particular in ribosomal nucleic acids. When use is made of hybridization probes which are specific for a nucleic acid sequence which is associated with antibiotic resistances, it is surprisingly possible, in the case of microorganisms from a biological sample, to make rapid and reliable predictions about the presence and/or strength of an antibiotic resistance, or the minimum inhibitory concentration for an antibiotic, on the basis of the appearance or absence of a hybridization in an in-situ detection method. The present invention enables the attending physician to obtain results in an incomparably rapid and specific manner, thereby increasing the safety of the therapy for the patient and enabling the costs of the entire treatment to be reduced substantially.

Part of the subject-matter of the present invention is consequently a process for detecting antibiotic resistances in microorganisms, which process comprises the steps of:
a) preparing a sample which contains microorganisms,
b) bringing the sample into contact with at least one hybridization probe, which is specific for a nucleic acid sequence in microorganisms which is associated with antibiotic resistances, under conditions which permit the probe to hybridize specifically, and
c) analyzing the sample in situ by determining the appearance or absence of a hybridization.

In a particularly preferred embodiment, several different hybridization probes are employed in the form of a mixture in the process according to the invention.

Surprisingly, these different hybridization probes bind, under identical hybridization conditions, to different target sequences with a specificity which is adequate for being able to detect a sequence difference of only one single base.

Preferably, the process according to the invention for detecting antibiotic resistances is used in bacterial organisms. The nucleic acid sequence which is associated with antibiotic resistances is selected, in particular, from ribosomal nucleic acid sequences, particularly preferably from bacterial 23S ribosomal nucleic acid sequences. Particular preference is given to using nucleic acid sequences from the peptidyltransferase center on the 23S RNA, the sequence of which (for *E. coli*) is depicted in FIG. 1.

Particularly preferably, the selected nucleic acid sequence encompasses a region corresponding to one or more of the nucleotides 2032, 2057, 2058, 2059, 2503 and 2611 on the *E. coli* 23S rRNA (numbering in accordance with Brosius et al., 1981), with mutations at these positions relating, in particular, to detecting resistances to macrolide antibiotics, e.g. clarithromycin and erythromycin. However, nucleic acid sequences from the 16S rRNA can also be detected, for example those nucleic acid sequences which mediate resistance to aminoglycoside antibiotics.

However, in addition to this, the process according to the invention is also suitable for detecting antibiotic resistances in other microorganisms, e.g. in protozoa. Organisms which particularly come into consideration in this regard are those which can be controlled by the administration of macrolide antibiotics, e.g. *Giardia lamblia*, a protozoan pathogen which is found in the upper small intestine in man and which is the causative agent of lamblia dysentery (Jablonowski et al., 1997), or *Pneumocystis carinii*, a protozoan organism which can give rise to a pneumonia of frequently fatal outcome in immunodeficient patients, e.g. in HIV patients.

The process according to the invention has a number of advantages as compared with known methods for detecting antibiotic resistances. Thus, in contrast to classical biochemical detection methods, the process according to the invention can also be used for rapidly investigating slowly growing pathogens or pathogens which are difficult to culture, or cannot be cultured, in vitro. In addition to this, because the detection is in situ, it is possible to locate the organisms directly in affected areas of tissue. As compared with other molecular biological methods such as PCR, the process according to the invention is distinguished by the fact that time-consuming and labor-intensive DNA preparation methods are dispensed with and that the detection method is less sensitive to inhibitors which may possibly be present in the sample material. Furthermore, the nucleic acid which is detected can be associated with bacterial morphologies such as cocci, rods, etc., a feature which results in an improvement in the reliability of the process. It is also possible to locate and quantify the pathogen in affected areas.

The process according to the invention is more specific and sensitive than other microscopic methods, e.g. staining methods (Gram, Grocott-Gomori, Giemsa). As compared with immunofluorescence methods, the smaller size of the probe is an advantage, which probe allows better penetration into the tissue, scarcely exhibits any nonspecific binding and is universally applicable and associated with lower costs.

The process according to the invention is suitable for all microorganisms, in particular pathogenic bacteria such as streptococci, *Bordetella* and *Corynebacterium*, and, in particular, for problematic microorganisms such as *Helicobacter* spec., e.g. *Helicobacter heilmannii* or *Helicobacter pylori*, mycobacteria, *Porphyromonas gingivalis, Propionibacterium acnes, Borrelia burgdorferi*, mycoplasmas, chlamydias and *Tropheryma whippelii* as well as representatives of the genera *Bratonella, Legionella, Nocardia* and *Actinomyces*, and also for other pathogenic organisms such as *Pneumocystis carinii* and *Giardia lamblia*.

A microorganism-containing sample is prepared in accordance with step (a) of the process according to the invention, preferably in the context of compiling results in human or veterinary medicine. While this sample can be any biological sample, it is preferably derived from human or animal tissues or body fluids, e.g. tissue sections, biopsies or blood samples. Surprisingly, the process according to the invention has such a high specificity and sensitivity that the sample can be investigated without the microorganisms being previously cultured or multiplied.

Particular preference is given to a presumptive medium being added to the sample prior to the investigation. This presumptive medium is a medium whose composition is adapted to the microbial flora of the clinical sample, in particular to the disease-causing organisms which may possibly be present, and conserves these organisms in a viable state for a limited period of time, e.g. from several hours to several days, but to a large extent suppresses growth of the organisms. Such a presumptive medium essentially consists of a special nutrient solution which is present, where appropriate, in a semisolid organic matrix, e.g. an agar matrix (Westblom et al., 1991). The nutrient solution contains a nitrogen source and essential components, such as trace elements, e.g. iron, zinc, manganese, vitamins, etc., which improve the stability of the isolated organisms. All the other constituents of this presumptive medium are preferably present in a buffered aqueous solution. The constituents of the nitrogen source are chemical or proteolytic digests of proteins of microbial, animal or vegetable origin, for example: peptones, tryptones or casitones or mixtures thereof, depending on the requirements of the selected microbial flora. In the case of anaerobic or microaerophilic organisms, reducing substances, such as reduced cysteine or thioglycolate, are admixed and/or oxygen-repelling additives are added to the medium.

Where appropriate, preparation of the sample can be additionally combined with an enrichment method, in particular when isolating organisms from liquid samples, e.g. blood or urine samples. The preferred enrichment method is based on binding the organisms to a solid matrix, in particular based on electrostatic interactions, e.g. to active charcoal or by way of defined ligands, such as polylysine, which are bound to a solid matrix. In accordance with the method, the blood flows, on withdrawal, into a sealed vessel, for example a syringe, which contains this matrix. After a brief incubation period, the blood is replaced by the above-mentioned presumptive medium, with the matrix-adsorbed organisms being conserved in a viable state in the sealed vessel.

Where appropriate, detection reagents, e.g. indicators which indicate the presence of pathogenic lead organisms within a short period of time, i.e. within minutes, can be added to the presumptive medium. This indicator can, for example, be a substrate mixture for a secreted lead enzyme (e.g. for the *Helicobacter* urease) whose conversion leads to a chromogenic product and/or indicates the production of characteristic substances such as particular toxins or metabolites. Prior to being examined for antibiotic resistances, the sample is also preferably fixed, e.g. with formaldehyde, paraformaldehyde or glutaraldehyde, and preferably permeabilized in order to enable the hybridization probes to penetrate more efficiently into the cells. The permeabilization method is directed toward the pathogen which is in each case being investigated, with suitable permeabilization methods having to be used in each case for Gram-negative bacteria and Gram-positive bacteria.

The hybridization probes may be nucleic acids such as DNA or RNA or else nucleic acid analogues or combinations of these. Preference is given to the hybridization probes being selected from nucleic acids such as DNA or nucleic acid analogues such as peptide nucleic acids (PNA).

The hybridization probes possess a hybridization region which is able to hybridize selectively with a target nucleic acid sequence in the microorganism. The length of this hybridization region preferably corresponds to from 10 to 30 nucleotide building blocks, particularly preferably from 15 to 20 nucleotide building blocks, in particular from 17 to 18 nucleotide building blocks.

The hybridization probes employed in the process according to the invention are particularly suitable for detecting mutations, e.g. mutations of individual nucleotides or short nucleotide segments, which are selected from deletions, transversions, transitions and modifications, e.g. methylations, of the corresponding wild type sequence.

The process according to the invention permits the use of a single hybridization probe. However, in many cases, it has proved advantageous to use a combination of several hybridization probes which are specific for different nucleic acid sequences associated with antibiotic resistances. The probes ClaR1 (SEQ ID NO. 10, ClaR2 (SEQ ID NO. 2) and ClaR3 (SEQ ID NO. 3) are examples of hybridization probes according to the invention which can be used for detecting macrolide resistances at positions 2058 and 2059 of the 23S RNA. These probes can be used either singly or in combination.

In order to increase the sensitivity of the process according to the invention, the hybridization probes which are specific for mutations associated with antibiotic resistances can be used in combination with one or more hybridization probes which are specific for a nucleic acid sequence which is associated with the wild type of the microorganism (i.e. an antibiotic-sensitive strain). ClaWT (SEQ ID NO. 4), which can, for example, be used in combination with the previously mentioned probes ClaR1, ClaR2 and ClaR3, is an example of such a hybridization probe.

The ratio of resistant organisms to sensitive organisms in a sample can be determined by using wild type-specific probes and antibiotic resistances [sic] mutant-specific probes which each carry different labeling groups.

Furthermore, it is additionally possible to use, in the process according to the invention, a hybridization probe which is specific for a species or genus of microorganisms. Hybridization probes of this nature are known and are preferably directed specifically against ribosomal nucleic acid sequences, e.g. 23S RNA, 16S RNA or ribosomal spacer sequences. Examples of these probes are hybridization probes which are directed against sequences from *H. pylori* 16S rRNA which are homologous with the *E. coli* regions 110–140 and/or 740–780, in particular the hybridization probes Hpy-1-16S-753 (SEQ ID NO. 5) and 120b (SEQ ID NO. 6), 585 (SEQ ID NO. 7) and 219 (SEQ ID NO. 8), which are used for the species-specific detection of *Helicobacter pylori*. Other examples of these probes [lacuna] which are specifically directed against sequences from *H. heilmanii* 16S rRNA which are homologous with the *E. coli* regions 580–610 and/or 640–670, in particular the hybridization probes Hh1 (SEQ ID NO. 9), Hh2 (SEQ ID NO. 10), Hh3 (SEQ ID NO. 11) and Hh4 (SEQ ID NO. 12) which are used for the species-specific detection of representatives of the *H. heilmanii* group.

The species-specific probes can also be used for detecting antibiotic-sensitive bacteria, in particular when using a probe mixture which contains, at one and the same time, probes for determining resistance and for determining the respective species. One such combined probe mixture can be used, for example, for detecting clarithromycin-resistant *Helicobacter* bacteria (both the resistance probe and the species-specific probe bind) or other clarithromycin-resistant bacteria (the resistance-specific probe binds) or antibiotic-sensitive *Helicobacter* bacteria (the resistance-specific probe does not bind and the species-specific probe does bind).

Preference is given, in the process according to the invention, to using hybridization probes which carry a direct label, i.e. one or more labeling groups are linked directly to the probe, preferably by means of covalent bonding. On the other hand, it is also possible to use indirectly labeled or labelable probes, e.g. probes which carry a biotin group which is in turn detected by binding streptavadin, with the streptavadin being linked to a suitable labeling group. Alternatively, the hybridization probes can also contain sequence regions which do not hybridize with nucleic acid sequences in the microorganism and which can be employed for hybridizing with a further, complementary, (directly or indirectly) labeled probe.

Any labeling groups per se can be used for the process according to the invention provided they enable the in-situ detection to be sufficiently sensitive. Preference is given to dye groups, fluorescence groups and/or enzyme groups. Fluorescence labeling groups are particularly preferred.

If several types of hybridization probe (e.g. several mutation-specific probes or one or more mutation-specific probes in combination with wild type-specific probes and/or species-specific probes) are used in the process according to the invention, it may be advantageous to employ different labeling groups, i.e. labeling groups which can be detected alongside each other. Thus, it is possible, for example when additionally using species-specific probes which possess a label which is different from that of the mutation-specific probe, to obtain, when both the probes hybridize at the same time, a third and different color which results from the two probe colors being mixed. If, for example, a green fluorophore, e.g. fluorescein, is chosen for the probes for determining the bacterial species, and a red fluorophore, e.g. rhodamine, is chosen for the probes for determining antibiotic resistance, the mixture of the two colors is then yellow. Using this probe combination, it is possible to determine the identity of the microorganism and the possible presence of an antibiotic resistance at one and the same time in one clinical sample. If the detected organism is antibiotic-sensitive, it can be reliably identified by the species-specific probe being bound on its own.

In addition to this, the process according to the invention even makes it possible to draw additional conclusions with regard to the minimum inhibitory concentration (MIC) of antibiotic-resistant microorganisms. Thus, it has been found that particular point mutations, or particular combinations of point mutations, correlate directly with the MIC values determined by conventional means. MIC values can therefore be determined by using hybridization probes which detect particular point mutations or particular combinations of these point mutations. For example, it is possible to use hybridization probes which are specially prepared for low, medium and high MIC values. This makes it possible for the attending physician to use precise doses of the antibiotic for the therapy.

The hybridization probe according to the invention is specific for a nucleic acid sequence in microorganisms which is associated with antibiotic resistances. This means that hybridization conditions exist under which the hybridization probe hybridizes to a nucleic acid sequence which is associated with antibiotic resistances but not to a corresponding nucleic acid sequence from an antibiotic-sensitive wild type organism. Depending on the base sequence of the hybridization probe and the target sequence, the skilled person can readily, by means of empirical investigations, ascertain hybridization conditions which are suitable for a particular test and which provide adequate specificity in distinguishing between wild type and mutated sequences. The hybridization buffer employed is preferably a buffer which contains from 0.5 to 1.5 M salt, e.g. NaCl, a detergent, SDS and formamide. Washing preferably takes place in a formamide-free buffer. The probes are selected such that the hybridization temperature is preferably in the range from 45 to 55° C.

The sample is evaluated in situ, preferably by microscopic methods, e.g. using a fluorescence microscope.

Another part of the subject-matter of the invention is the use of an in-situ nucleic acid hybridization process for detecting antibiotic resistances in microorganisms, in particular in bacteria. The nucleic acid hybridization process is preferably carried out as previously described. The process is particularly suitable for detecting resistances to macrolide antibiotics. However, the process is also suitable for detecting antibiotic resistance mechanisms directed against lincosamide, aminoglycoside/aminocyclitol, tetracycline and chloramphenicol antibiotics and which are based on changes in ribosomal RNA sequences.

Particular preference is given to detecting resistances to macrolide antibiotics selected from the group consisting of clarithromycin, erythromycin, azithromycin and roxithromycin. In addition, particular preference is also given to detecting resistances to aminoglycoside antibiotics selected from the group consisting of streptomycin, neomycin, paromomycin, kanamycin, gentamicin, tobramycin, amikacin, netilmicin and sisomicin.

Yet another part of the subject-matter of the present invention is a reagent kit for typing microorganisms and/or detecting antibiotic resistances in microorganisms. In a first embodiment, this reagent kit is based on detection by in-situ hybridization and comprises:
(a) means for preparing the sample, and
(b) at least one hybridization probe which is specific for a nucleic acid sequence in microorganisms which is associated with antibiotic resistances, and/or at least one hybridization probe which is specific for a species or genus of microorganism.

The means for preparing the sample preferably comprise a presumptive medium which can have a composition as previously indicated. Alternatively, or in addition, the means for preparing the sample can also comprise means for enriching microorganisms, e.g. an adsorption matrix for enriching organisms from a liquid sample, solutions or suspensions for fixing the sample, and hybridization buffer and/or washing buffer. The hybridization probes are preferably labeled as previously described.

According to a second embodiment according to the invention, the reagent kit for typing microorganisms and/or detecting antibiotic resistances in microorganisms comprises
(a) a presumptive medium for microorganisms, and
(b) means for typing and/or detecting antibiotic resistances.

According to this embodiment, the means for typing and/or for detecting antibiotic resistances are not restricted to using hybridization probes and other hybridization reagents. It is also possible to conceive of indicator substances which indicate the presence of microorganisms, e.g. urease detection reagents for *Helicobacter* spec., e.g. *H. heilmannii* and/or *H. pylori*, hemolysin reagents for streptococci, and reagents for detecting toxins produced by *Clostridium difficile, Corynebacterium diphtheriae* and *Bordetella pertussis*. Preference is given to the reagents for typing microorganism species or genera already being dissolved or suspended in the presumptive medium such that the kit contains a presumptive medium with combined indicator system. It is also conceivable for the presumptive medium with combined indicator system to be additionally combined with an enrichment method. In this case, the organisms are enriched from body fluids, for example blood, in a first step and treated, in a second step, with the indicator-containing presumptive medium. In addition, the kit can contain, where appropriate in separate form, means for detecting antibiotic resistances, e.g. the previously described hybridization probes, and suitable buffers.

In addition to this, the invention relates to the use, for the species-specific detection of *Helicobacter pylori* and/or *Helicobacter nemestriniae*, of an oligonucleotide having a nucleotide sequence which is complementary to the 16S rRNA region of *H. pylori* which corresponds to *E. coli* 16S rRNA positions 110 to 140 (in particular 120 to 137), 740 to 780 (in particular 753 to 770), 580–610 (in particular 585–605) or 210–245 (in particular 219–240). It was ascertained, surprisingly, that, when used as amplification primers or hybridization probes, such oligonucleotides, i.e. nucleic acids or nucleic acid analogues having a length of preferably from 10 to 30 nucleotide building blocks, exhibit a significantly higher specificity with regard to recognizing different *H. pylori* isolates than do other sequences and, in addition to this, enable *H. pylori* and other related species to be differentiated reliably. Preference is given to using an oligonucleotide which contains the sequences depicted in SEQ ID NO. 5, 6, 7 or 8 or at least a part region thereof which is 10 nucleotides in length. In addition, the invention relates to the use, for specifically detecting representatives of the *H. heilmannii* group, of an oligonucleotide having a nucleotide sequence which is complementary to the 16S rRNA region of *H. heilmannii* which corresponds to *E. coli* 16S rRNA positions 580–610 and/or 640–670. Preference is given to using an oligonucleotide which contains the sequences depicted in SEQ ID NO. 9, 10, 11 or 12 or a part region thereof which is at least 10 nucleotides in length.

The oligonucleotide preferably carries a labeling group. The species-specific substances can be employed on their own for identifying the organism. In addition, the species-specific probes can also be employed in combination with the detection of antibiotic resistances. Preference is also given to employing two or more species-specific probes in a test, with this ensuring that less biologically active *Helicobacter* cells, which as a rule contain a lower number of ribosomes, are also detected.

Yet another part of the subject-matter of the invention is the use of an oligonucleotide from a bacterial 23S rRNA, in particular from a region which contains the peptidyltransferase center, for detecting antibiotic resistances. Preference is given to using oligonucleotides which are specific for a mutation of the wild type sequence which is associated with antibiotic resistances and encompass a region corresponding to one or more of the nucleotides 2032, 2057, 2058, 2059, 2503 and 2611 on the *E. coli* 23S rRNA. Particular preference is given to using oligonucleotides having the sequence depicted in SEQ ID NO. 1, SEQ ID NO. 2 or SEQ ID NO. 3. Where appropriate, these antibiotic resistance-specific oligonucleotides can be used together with a wild type-specific oligonucleotide which is directed against the same region as is the resistance-specific probe. The wild type-specific oligonucleotide preferably has the sequence depicted in SEQ ID NO. 4.

Consequently, the present invention also relates to oligonucleotides, i.e. nucleic acids and/or nucleic acid analogues, which contain the sequence depicted in SEQ ID NO. 1, 2, 3, 4, 5, 6, 7, 8, 10, 11 or 12 or at least a part region thereof which is 10 nucleotides in length. The invention also relates to compositions which contain two or more of said oligonucleotides. One or more of the oligonucleotides preferably carry a labeling group.

The invention is explained further by means of the following figures and examples.

Figure 1:
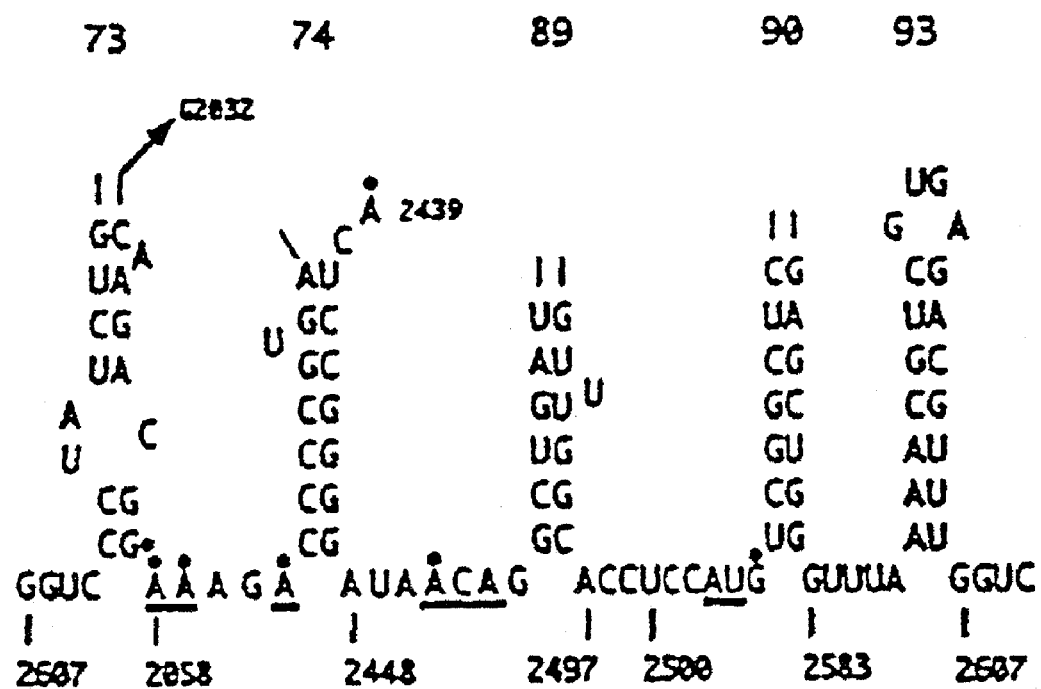
FIG. 1 shows a diagram of the peptidyltransferase center in bacterial 23S rRNA. The diagram is a linear representation in which the positions at which resistance mutations have already been found are indicated by underlining. Filled circles represent the footprints of erythromycin. The upper numbers relate to the helix numbering according to Brimacombe and the lower numbers relate to the nucleotide position in E. coli according to Brosius.

SEQ ID NO. 1–12 show the nucleotide sequences of the probes ClaR1 (1), ClaR2 (2), ClaR3 (3), ClaWT (4), Hpyl-16S-753 [sic] (5), 120b (6), Hpyl-16S-585 (7) and Hpyl-16S-219 (8), Hh1 (9), Hh2 (10), Hh3 (11) and Hh4 (12).

EXAMPLES

Example 1

Developing a combination of *H. pylori*-specific and *H. heilmannii*-specific probes for the in-situ hybridization for detecting antibiotic-sensitive *Helicobacter* bacteria.

An alignment comprising 108 almost complete 16S rRNA sequences from organisms from the ε group of proteobacteria (including 50 *Helicobacter* sequences, in turn including 10 *H. pylori* sequences) was used as a reference for deriving specific *H. pylori* probes (Neefs et al., 1993). This resulted in the assignment of a total of 4 potential target sequence regions, from which a variety of probe prototypes were derived for further testing. The testing of the different probe prototypes in an in-situ hybridization is an important element in the strategy for developing probes. Data are availabe which suggest that certain regions of the ribosomal RNA are not available for the in-situ hybridization reaction. Stable secondary structures and the occupation of probe-binding sites by ribosomal proteins have been discussed as possible causes for this (Amann et al, 1995; Frischer, 1996). In particular, this testing has to be used to find the probe sequences which exclude the species which are most closely related to *H. pylori*, such as *H. mustelae, H. fells, H. fenneliae, C. coli, C. jejuni* and *W. succinogenes* (see Table 5). The in-situ hybridization method employed in the testing is described in detail in Example 2 below.

It was finally possible to determine, in each region, a segment which was effective for probe construction, with the probes Hpyl-16S-753, Hpyl-165-120b [sic], Hpyl-16S-585 and Hpyl-16S-219 being respectively located in these segments. Further extensive in-situ binding studies carried out on clinical samples showed two probe sequences to be particularly effective: Hpyl-16S-585 and Hpyl-16S-219. Hpyl-16S-585 is directed against a region of the 16S rRNA sequence which only occurs in *H. pylori* and *H. nemestrinae* and is not found in other bacterial species (Table 3). The probe Hpyl-16S-219 is directed against another region which is specific for *H. pylori*. The two probes were provided either with the fluorescence dye fluorescein (emits green fluorescence) or the fluorescence dye Cy3 (emits red fluorescence) by way of an amino linker at the 51 end. It is particularly important to use both probes simultaneously for detecting *H. pylori* in situ, in order to detect *H. pylori* cells which are metabolically less active. As a rule, bacteria whose metabolism is reduced have a lower content of ribosomes or rRNA, resulting in the detection method losing sensitivity, particularly when only one probe is used and this probe is provided with fluorescein, which is a dye which only emits comparatively weakly.

In addition, it was also possible to identify, from the 16S rRNA, the detection probes Hh1, Hh2, Hh3 and Hh4 which were specific for *H. heilmannii* (Table 3).

Table 3: Nucleotide Sequences of Different Probes for Determining Helicobacter Pylori and Helicobacter Heilmannii and for Determining Macrolide Resistances on Bacterial 23S rRNA

| Name | Probe Sequence (5' – 3') | Target region* rRNA | Binding Specificity |
|---|---|---|---|
| Hpyl-16S-753 | GCTTTCGCGCAATGAGCG SEQ ID No: 5 | 753–770 (16S) | H. pylori |
| 120 b | AGGCACATGATCTATGCG SEQ ID No: 6 | 120–137 (16S) | H. pylori |
| Hpyl-16S-585 | CACACCTGACTGACTATCCCG SEQ ID No: 7 | 585–605 (16S) | H. pylori H. nemestrinae |
| Hpyl-16S-219 | GGACATAGGCTGATCTCTTAGC SEQ ID No: 8 | 219–240 (16S) | H. pylori |
| Hh1 | CCCACACTCCAGAAG (G/A) ATAG SEQ ID No: 9 | 644–663 (16S) | H. heilmannii |
| Hh2 | CCCACACTCTAGGGTT (G/T) GCAG SEQ ID No: 10 | 644–664 (16S) | H. heilmannii |
| Hh3 | CCCACACTCTAGAAAGATAG SEQ ID No: 11 | 644–663 (16S) | H. heilmannii |
| Hh4 | CACATCTGACTTGCCACCCCG SEQ ID No: 12 | 585–605 (16S) | H. heilmannii |
| ClaR1 | CGGGGTCTTCCCGTCTT SEQ ID No: 1 | 2051–2067 (23S) | A2058G (Cla$^R$) |
| ClaR2 | CGGGGTCTCTCCGTCTT SEQ ID No: 2 | 2051–2067 (23S) | A2059G (Cla$^R$) |
| ClaR3 | CGGGGTCTTGCCGTCTT SEQ ID No: 3 | 2051–2067 (23S) | A2058C (Cla$^R$) |
| ClaWT | CGGGGTCTTTCCGTCTT SEQ ID No: 4 | 2051–2067 (23S) | Wild type (Cla$^R$) |

For testing the probes, different reference cells were fixed with 3% buffered paraformaldehyde solution, as described in Amann et al., and immobilized on microscope slides by means of air drying (Amann et al., 1990).

5 ng of the probe are incubated with these microscope slides at 46° C. for 90 min, in a hybridization buffer (0.9 M NaCl, 0.02 M tris/HCl, pH 8.0, 0.01% SDS, 20% formamide). The slides are then washed for 15' at 48° C. (0.25 M NaCl, 0.02 M tris/HCl, pH 8.0, 0.01% SDS). Excess washing buffer is removed from the microscope slides with PBS and the slides are embedded in Citifluor AF1 (Citifluor Ltd., London, UK) in order to decrease color-fading effects. The hybridization is analyzed using an epifluorescence microscope (standard filters for red and green fluorescence). Under the given conditions, all the *H. pylori* strains which have so far been tested (16/16) hybridized with the probe Hpyl-16S-753 whereas cells from other *Helicobacter* species and other reference strains (6/6) did not bind to the probe (Table 4). These other *Helicobacter* species and further reference strains were the species which are most closely related to *Helicobacter pylori*, i.e. *H. mustelae, H. felis, H. fennelliae, C. coli, C. jejuni* and *W. succinogenes* (Table 4). Probe 120b reacted with 11 out of 16 strains and thereby displayed a somewhat lower specificity with regard to recognizing different *H. pylori* isolates (Table 4).

TABLE 4

Testing the specificity of two *H. pylori* probes

| Strain | Probe 120b2 (red) | Hpyl-16S-753 (red) |
|---|---|---|
| *H. pylori* P1 | ++ | ++ |
| *H. pylori* P79 | ++ | ++ |
| *H. pylori* P79B6.1 | n.d. | n.d. |
| *H. pylori* P2 | ++ | ++ |
| *H. pylori* P8 | ++ | ++ |
| *H. pylori* P12 | – | ++ |
| *H. pylori* P80 | n.d. | n.d. |
| *H. pylori* P80B6.1 | – | ++ |
| *H. pylori* P21 | ++ | ++ |
| *H. pylori* P27 | ++ | ++ |
| *H. pylori* P29 | ++ | ++ |
| *H. pylori* P31 | ++ | ++ |
| *H. pylori* P49 | ++ | ++ |
| *H. pylori* P76 | ++ | ++ |
| *H. pylori* P66 | ++ | ++ |
| *H. pylori* P92' | – | ++ |
| *H. pylori* P106 | – | ++ |
| Cl<sup>r</sup> | – | ++ |
| *Helicobacter musteleae* NCTC12032 | n.d. | – |
| *Helicobacter felis* ATCC49179 | n.d. | – |
| *Helicobacter fennelliae* | n.d. | – |
| *Campylobacter coli* | n.d. | – |
| *Campylobacter jejuni* | n.d. | – |
| *Wolinella succinogenes* | n.d. | – |

++, good hybridization; –, no hybridization

Example 2

Using rRNA-directed, fluorescence-labeled oligo-nucleotide probes for the in-situ detection of clarithromycin-resistant *H. pylori*.

Three different mutations in the 23S rRNA have by now been described which are able to mediate resistance to the macrolide clarithromycin (Versalovic et al., 1997). According to the information in this article, clarithromycin resistances can be caused by an A⇒G transition either in position 2058* (*nomenclature according to Brosius) or 2059*, or by an A⇒C transversion at position 2058*. In order to be able to detect all three resistance-mediating point mutations at one and the same time, three different probe sets were constructed, with these probe sets covering the abovementioned region in different ways. In view of the special requirements of an in-situ hybridization, the in-situ binding properties of the different probe sets were tested in a manner analogous to that used for the *H. pylori*-specific probes (see Example 1). The crucial selection criteria were as follows: (1) unambiguous detection of each respective point mutation, (2) simultaneous detection of the point mutation and of the *H. pylori*-specific rRNA segments by simultaneously using the probes identified in Example 1.

It was finally possible to identify three probes which were effective for detecting the three resistance-mediating mutations in situ: ClaR1, ClaR2 and ClaR3. The probes ClaR3 and ClaR3. [sic] The probes ClaR1 and ClaR3 are complementary to the rRNA which is altered at position 2058*, whereas probe ClaR2 is complementary to the rRNA which is mutated at position 2059*. The probes were provided either with the fluorescence dye fluorescein (emits green fluorescence) or with the fluorescence dye Cy3 (emits red fluorescence) by way of an amino linker at the 5' end. It is advantageous to label the probes with the more strongly emitting fluorescence dye Cy3 since this ensures more sensitive detection, particularly when the cells are *H. pylori* cells which are metabolically less active (see above).

The above-described probes were used to test suitable conditions and finally verify them on a total of 20 clarithromycin-resistant and 15 clarithromycin-sensitive *H. pylori* strains. It was possible to demonstrate unambiguously that the resistance detection was specific for *H. pylori*, since the two probes H. pyl-16S-219 and Hpyl-16S-585 reacted with all the *H. pylori* strains examined, whereas none of the related *Helicobacter* species was detected. ClaR1 recognizes the mutation A2058G (Cla$^R$), ClaR2 recognizes the mutation A2059G (Cla$^R$) and ClaR3 recognizes the mutation A2058C (Cla$^R$).

A resistance determination should preferably be carried out using all five probes (ClaR1–3; Hpyl-16S-585; Hpyl-16S-219), since this achieves optimum analytical power (see below). In this embodiment, it has proved advantageous to detect the point mutations in a competitive hybridization assay and in this way ensure that this detection is specific. To this end, a probe was additionally admixed with the probe mixture, with this probe being complementary to the wild type sequence in the region of the resistance-mediating mutations. The sequence of the probe ClaWT was ascertained after appropriate tests. The three Cy3-labeled probes ClaR1, ClaR2 and ClaR3 are used together with an equimolar quantity of the unlabeled ClaWT probe. In order, at the same time, to indicate the identity of the bacteria which are present, the two FLUOS-labeled *H. pylori*-specific probes are used in addition. The following conclusions can therefore be drawn in accordance with the application form described:

1. Yellow fluorescence signal (color obtained from mixing red (resistance) and green (*H. pylori*)=clarithromycin-resistant *H. pylori*
2. Green fluorescence signal=clarithromycin-sensitive *H. pylori*
3. Red fluorescence signal=clarithromycin-resistant bacterium of unknown nature.

The probe mixture employed was found to be 100% specific under the following hybridization conditions:
Hybridization: 90 minutes at 46° C. in 0.9 M NaCl; 0.02 M tris/HCl, pH 8.0; 0.01% SDS; 20% formamide.

Washing step: 15 minutes at 48° C. in 0.25 M NaCl; 0.02 M tris/HCl, pH 8.0; 0.01% SDS

TABLE 5

Testing of the individual identified probes on various bacterial strains and on stomach biopsies (antrum) by in-situ hybridization

| Sample composition | Number[1] | Hypl-16S-585 | ClaR1 | ClaR2 | ClaR3 | WT | EUB |
|---|---|---|---|---|---|---|---|
| A) Bacterial strains | | | | | | | |
| H. pylori | 35 | 35 | 6 | 12 | 2 | 15 | 35 |
| H. mustelae | 1 | 0 | 0 | 0 | 0 | 1 | 1 |
| H. felis | 1 | 0 | 0 | 0 | 0 | 1 | 1 |
| H. fenneliae | 1 | 0 | 0 | 0 | 0 | 1 | 1 |
| Campylobacter jejuni | 1 | 0 | 0 | 0 | 0 | 1 | 1 |
| C. coli | 1 | 0 | 0 | 0 | 0 | 1 | 1 |
| Wollinella succinogenes | 1 | 0 | 0 | 0 | 0 | 1 | 1 |
| B) Stomach biopsy samples | 27[2] | 17 | 4 | 4 | 0 | 13 | 17 |

[1]total number of strains examined
[2]total number of biopsy samples examined. 2 H. pylori strains were detected in one biopsy sample, i.e. a clarithromycin-resistant strain and a clarithromycin-sensitive strain.

Example 3

Determining the clarithromycin resistance of *H. pylori* in situ in tissue sections.

The possibility of determining the resistance of *H. pylori* in situ in tissue sections was first of all evaluated in an animal model. 6–8-week-old C57B16 mice were infected orally with 10 colony-forming units of the *H. pylori* strain P76. The mouse was killed 4 days after the infection and the stomach was removed under sterile conditions. The stomach was chopped into small pieces with a scalpel and the pieces were placed in a 3% solution of paraformaldehyde for 12 h. This was then followed by two washing steps, of one hour in each case, in a buffered salt solution, e.g. PBS. The material was then placed in a frozen section medium, after which it was all frozen at −70° C. Finally, frozen sections, which were each 5–10 μm in thickness, were prepared from the frozen material using a cryomicrotome and fixed on polylysine-coated microscope slides. Carrying out the detection reaction in accordance with the above-described conditions then gave a positive result, such that it was possible to clearly detect the individual *H. pylori* organisms on the inner side of the crypt in the stomach sample.

In continuing the investigation, use was now made of paraffin sections of stomach biopsies taken from chronically infected humans whose microbiological background had been determined beforehand using conventional methods. The tissue sections were examined in accordance with the standard protocol, with the two FLUOS-labeled *H. pylori*-specific probes, the Cy3-labeled probes ClaR1, ClaR2 and ClaR3, and the unlabeled ClaWT probe all being employed. A total of 27 stomach biopsy samples was examined, with an *H. pylori* infection being diagnosed correctly, i.e. in agreement with the conventional method, in 17 cases. A clarithromycin resistance was detected correctly in 5 cases. A mixed infection of *H. pylori*, consisting of clarithromycin-resistant strain and clarithromycin-sensitive strain, was even detected in one case (see Table 5).

In another application form, the stomach biopsies are not fixed and worked up histologically; instead, they are transferred into a special transportation and/or presumptive medium which ensures that the organism survives over a long period and indicates the presence of *H. pylori* in the sample, where appropriate (see Example 5). If samples are removed from the transportation medium after storage times of differing lengths and examined using the above-described process, it is surprisingly still possible to characterize the bacteria unambiguously after 7 days. The finding that the sample did not necessarily have to be stored in the cold (4° C.) for this was particularly surprising.

TABLE 6

Culturing and hybridization results obtained for *H. pylori* Hpci 001-Tübingen after transportation in CREATOGEN transportation medium for differing lengths of time

| Detection of *H. pylori* from transportation media | Storage at room temperature | | Storage at 4° C. | |
|---|---|---|---|---|
| | Conventional culture | In-situ hybridization | Conventional culture | In-situ hybridization |
| 6 h | + | + | + | + |
| 1 day | + | + | + | + |
| 2 days | − | + | + | + |
| 3 days | − | + | + | + |
| 4 days | − | + | + | + |
| 7 days | − | + | − | + |

− not detected
+ detected

Example 4

Comparing the 23S rRNA sequences of different medically important bacteria within the clarithromycin resistance region.

The computer program ARB (Ludwig et al., Munich Technical University) was used to compare the 23S rRNA from 40 Gram-positive and Gram-negative bacteria with the macrolide resistance-mediating region of *H. pylori* (Table 6). In all the bacteria examined, the results show strong conservation of the primary structure of this special region of the ribosomal RNA in which resistance to macrolide antibiotics is determined. However, the binding specificity of the identified probes ClaR1, ClaR2 and ClaR3 for *H. pylori* appears to be met. Since the 40 sequences from the database are probably sequences from clarithromycin-sensitive bacteria, and it can be assumed that clarithromycin resistance in these bacteria, as in *H. pylori*, is also determined by a mutation in positions 2058/2059 of the 23S rRNA (in accordance with Brosius), the above-described process for determining macrolide resistances in situ can also be employed in the case of these bacteria. It is only necessary, for unambiguously classifying the corresponding pathogenic organism which is linked to the pathogenic process, to derive a species-specific probe and to combine this probe, in the manner described, with the probe mixture for identifying the resistance-mediating mutation.

TABLE 7

Comparison of the 23S rRNA sequences of various bacterial species within the clarithromycin resistance region

| | | |
|---|---|---|
| Probe sequence | 5'-CGGGGTCTTTCCGTCTT-3' | SEQ ID No: 4 |
| rRNA sequence | mis 5'-AAGACGGAAAGACCCCG-3' | SEQ ID No: 13 |

| Species | mis | Sequence |
|---|---|---|
| Helicobacter pylori claWT | 0 | ACCCGCGGC-==================-UGGACCUUU |
| Helicobacter pylori claR1 | 1 | ACCCGCGGC-========G==========-UGGACCUUU |
| Helicobacter pylori claR2 | 1 | ACCCGCGGC-=========G=========-UGGACCUUU |
| Helicobacter pylori claR3 | 1 | ACCCGCGGC-=========C=========-UGGACCUUU |
| Campylobacter jejuni | 0 | ACCCGCGGC-==================-UGGACCUUU |
| Campylobacter coli | 0 | ACCCGCGGC-==================-UGGACCUUU |
| Wolinella succinogenes | 0 | ACCCGCGGC-==================-UGGACCUUU |
| Nannocystis exedens | 0 | ACCCGCGGC-==================-UGAACCUUU |
| Escherichia coli | 0 | ACCCGCGGC-==================-UGAACCUUU |
| Salmonella typhi | 0 | ACCCGCGGC-==================-UGAACCUUU |
| Enterobacter cloacae | 0 | ACCCGCGGC-==================-UGAACCUUU |
| Citrobacter freundii | 0 | ACCCGCGGC-==================-UGAACCUUU |
| Klebsiella pneumoniae | 0 | ACCCGCGGC-==================-UGAACCUUU |
| Yersinia pestis | 0 | ACCCGCGGC-==================-UGAACCUUU |
| Plesiomonas shigelloides | 0 | ACCCGCGGC-==================-UGAACCUUU |
| Haemophilus influenzae | 1 | ACCCGCGGC-U================-UGAACCUUU |
| Vibrio vulnificus | 1 | ACCCGCGGC-U================-UGAACCUUU |
| Aeromonas hydrophila | 1 | ACCCGCGGC-U================-UGAACCUUU |
| Pseudomonas aeruginosa | 1 | AUCCGCGGC-U================-UGAACCUUU |
| Acinetobacter calcoaceticus | 1 | ACCCGCGGC-U================-UGAACCUUU |
| Neisseria meningitidis | 1 | ACCCGCUGC-U================-UGAACCUUU |
| Bordetella pertussis | 2 | ACCCGCGGC-U================A-UGAACCUUU |
| Bartonella bacilliformis | 1 | UCCUGCGGU-U================-UGCACCUUU |
| Rickettsia rickettsii | 1 | UCCCGCGGU-C================-UGAACCUUU |
| Borrelia burgdorferi | 1 | ACUUGUGGU-U================-UGAACCUUU |
| Leptospirillum ferrugineum | 2 | CCCCGCGGC-U================-UGCACCUUU |
| Listeria monocytogenes | 1 | ACCCGCGAC-=G===============-UGGACCUUU |
| Staphylococcus aureus | 1 | ACCCGCGAC-=G===============-UGGAGCUUU |
| Bacillus anthracis | 1 | ACCCGCGAC-=G=============N=-UGGACCUUU |
| Mycoplasma hyopneumoniae | 1 | ACCCGCAUC-======A==========-UGGAGCUUU |
| Mycoplasma pneumoniae | 2 | AGGCGCAAC-GG===============-UGAAGCUUU |
| Streptococcus parauberis | 2 | ACCCGCGAC-=G==============A-UGGACCUUU |
| Lactococcus lactis | 2 | ACCCGCGAC-=G==============A-UGGAGCPUU |
| Enterococcus faecalis | 2 | ACCCGCGAC-=G==============A-UGGAGCUUU |
| Clostridium botulinum | 2 | ACCCGCGAU-UG==============-UAGAGCUUU |
| Streptomyces griseus | 1 | UCGCGCAGC-=G===============-GGACCUUA |
| Micrococcus luteus | 1 | ACGCGCAGA-=G===============-UGACCUUUA |
| Corynebacterium glutamicum | 1 | ACGCGCGGC-=G===============-GGACCUUCA |
| Gardnerella vaginalis | 1 | AAGCGCAGA-=G===============-GGACCUUUA |
| Mycobacterium leprae | 2 | ACGUGCGGC-=G====A==========-GGACCUUCA |
| Bifidobacterium bifidum | 2 | AAGCGCAGA-=G====A==========-GGACCUUUA |
| Chlamydia trachomatis | 2 | ACCCGCGAA-=G====A==========-UGAACCUUU |
| Chlamydia pneumoniae | 2 | CCCCGCAAA-=G====A==========-UGAACCUUU |
| Bacteroides fragilis | 3 | ACCCGCGAU-G====A==========-UGAACCUUU | mis, number of mismatches with the rRNA sequence in this region. The starting position of the probe sequence in the 23S rRNA of the different species corresponds to position 2051 in *E. coli* (Brosius et al., 1981), N, corresponds to A, C, G or T.=identical to the rRNA sequence.

Example 5

Developing a presumptive medium for bacterial gastritis combined with urease detection especially for *Helicobacter pylori*.

The particular aim is to develop a presumptive medium which should make it possible to conserve viable *Helicobacter pylori* bacteria from stomach biopsies, ideally over a period of 5 days but at least over 48 hours. In addition, the accompanying flora, if present, should be preserved in order to ensure that the microbiological evaluation is complete. The growth of the organisms must be restricted in order to keep the fractional composition of the organisms in the biopsy as unaltered as possible. The presumptive medium essentially consists of a buffered nutrient solution which is preferably present in a semisolid organic matrix, such as (0.2–1.5%) agar or (at least 15%) gelatin. The nutrient solution contains a nitrogen source and further essential components which improve the stability of *Helicobacter*. The nitrogen source takes up from 0.5 to 5% of the presumptive medium. It consists of chemical or proteolytic digests of proteins of microbial, animal or plant origin, such as peptones, tryptones or casitones or mixtures of these compounds. Particular preference is given to media such as Schivo-Medium® or brain-heart infusion (BHI)-based media. Other preferred constituents are yeast extract (e.g. 0.01%), serum proteins, such as horse serum or fetal calf serum or bovine serum albumin, and defined organic substances, such as 2,6-dimethyl-beta-cyclodextrin and cholesterol. The serum proteins should take up 1–10% of the presumptive medium, with the organic substances taking up 0.01–0.2%. In addition, reduced cysteine or thioglycolate are admixed with the presumptive medium and/or oxygen-repelling additives are added to it. All the components are present in a buffered, aqueous solution whose preferred pH is between 5.5 and 6.5. The biopsy sample is introduced into the lower third of the semisolid matrix thereby preventing atmospheric oxygen from diffusing in, an arrangement which improves the survival conditions for the organism.

Combining the presumptive medium with a urease detection test is novel. It offers the physician the advantage that he is given a rapid indication of a possible *Helicobacter* infection and can directly initiate further measures. To this end, (0.5–5%) urea and (0.001–0.01%) phenol red, or other pH indicators, such a bromcresol purple, are also added to the presumptive medium. The transformation of the urea by urease leads, inter alia, to the production of ammonia, which makes the pH basic and, for example, changes the pH indicator phenol red from yellowish into red to violet. The speed of the color change, the intensity of the color, and the coloration, correlate directly with the quantity of urease-producing bacteria. The constituents of the combined presumptive medium are adjusted such that high sensitivity is achieved (500–2000 organisms/presumptive medium) and autolysis of the organisms is suppressed. Alternatively, a synthetic urease substrate, whose transformation brings about a color change, can be admixed with the presumptive medium.

Comparative investigations provide evidence that other, routinely employed urease detection methods lead to rapid lysis of the organisms. This is of the greatest importance since more recent investigations show that other urease-producing organisms, such as *Proteus mirabilis, Klebsiella oxytoca* and *Pseudomonas aeruginosa*, are frequently to be found in the biopsy samples. In contrast to *Helicobacter*, these organisms do not secrete any urease; instead the enzyme is present inside the cell. In our own investigations, we have established that the bacteria are lysed in current urease detection methods such as the CLO test, with the intracellular urease being released and immediately reacting with the substrate which is now available. In a provisional investigation carried out on 32 patients suffering from acute gastritis, it was only possible, when conventional methods were used, to isolate a *Helicobacter* from 34% of the biopsies which were examined microbiologically. In this connection, the possibility cannot be ruled out that the *Helicobacter*-free biopsies were colonized with strains which are very difficult to culture. However, it is significant that a major part (>50%) of the *Helicobacter*-free biopsies contained other urease-producing organisms which were detected by the currently employed methods for detecting urease. The combined transportation and indicator medium delays or prevents lysis of these bacteria and consequently guarantees that the detection of urease is *Helicobacter*-specific.

TABLE 8

| Urease-producing organism[1] | Change in color of the presumptive medium[2] | |
|---|---|---|
| | 5 hours | 24 hours |
| *Helicobacter pylori* | ++ (<10 minutes) | +++ |
| *Proteus mirabilis* | +/− (>3 hours) | ++ |
| *Klebsiella oxytoca* | − | − |
| *Pseudomonas aeruginosa* | − | − |

[1]One complete bacterial colony was used for each test.
[2]The presumptive medium was incubated at room temperature (21–25° C.) and evaluated visually.

Example 6

Testing clarithromycin-resistant *H. pylori* strains for antibiotic sensitivity by means of in situ detection with rRNA-directed fluorescence-labeled probes.

Based on the observation made by Versalovic et al. (1997) that the different resistance-mediating point mutations on the 23S rRNA correlate with the sensitivity of the organism to clarithromycin, the possibility arises, from the present, novel results, of directly testing for antibiotic sensitivity by using the individual probes (ClaR1–3).

Thus, mutations in position A2058G lead to significantly higher resistance values than do mutations in position A2059G. As has previously been demonstrated, the probe ClaR1 detects the mutation in position A2058G specifically. In an optimization process, highly specific detection of the A2058G point mutation was achieved with a mixture consisting of the Cy3-labeled ClaR1 probe and the unlabeled probes ClaWt and ClaR3.

A functional probe mixture for specifically detecting the A2059G point mutation, and consisting of the Cy3-labeled ClaR2 probe and the unlabeled ClaWT probe, was developed in a similar manner. The Cy3-labeled probe Cla3 is used in combination with the unlabeled probe ClaWT for detecting the point mutation A2058C.

The hybridization is carried out in the buffer mentioned in Example 2. If the test for antibiotic sensitivity is to be coupled with the identification of *H. pylori*, the FLUOS-labeled oligonucleotides Hpyl-16S-585-FLUOS and Hpyl-16S-219-FLUOS are then also added to the abovementioned probe combinations.

Table 8:

Evaluating the MIC value determination by in-situ hybridization using conventionally characterized *H. pylori* isolates.

| Species | Strain | ClaR1 | ClaR2 | ClaR3 | Hpyl-16S-585 | MIC value (mg/l) |
|---|---|---|---|---|---|---|
| *H. pylori* | MPS1726 | + | − | − | + | >256 |
| | MPS1765 | + | − | − | + | >256 |
| | MC141 | + | − | − | + | >256 |
| | MPS3286 | − | − | + | + | >256 |
| | MPS3137 | − | + | − | + | 96 |
| | FD591 | − | + | − | + | 16/32 |
| | KJ472 | − | + | − | + | 16 |
| | HH531 | − | + | − | + | 48 |
| | MC028 | − | + | − | + | 24 |
| | MC132 | − | + | − | + | 12 |

− no fluorescence signal detectable.
+ clear fluorescence signal detected

Example 7

The overall process for determining resistance is composed of two successive constituent steps, i.e. the isolation of the sample (A) and the detection reaction (B).

Sample isolation essentially comprises specifically isolating biological material which has been colonized by the disease-causing organism. The biological material which has been obtained can then be directly supplied to the detection reaction, or fixed using known methods, or transferred into a special presumptive medium (see Example 5).

The detection reaction (in situ hybridization) essentially requires three procedural steps, i.e. (1) immobilization of the sample on a support, (2) permeabilization of the sample, and (3) the actual hybridization reaction and its evaluation.

In the case of microscopic examination, the sample is immobilized on a microscope slide which is as a rule made of glass. It is also possible to use other support materials, e.g. microtiter plates or films or silicon plates depending on the form of investigation selected. As a rule, the sample is applied to the microscope slide in the form of a smear. In the case of tissue samples, preference is given to using sections. Finally, the sample is immobilized on the microscope slide by means of air drying (Amann et al., 1990), with it being possible to improve the fixing of the sample by pretreating the microscope slide, e.g. with polylysine or even specific receptor molecules such as antibodies.

The permeabilization step makes the sample, in particular the bacteria which are present in the sample, permeable to the probes. The process is designed such that it is in particular the bacterial coat which is made permeable, with the internal structure being to a large extent preserved. As a rule, a conventionally implemented fixing method is sufficient for permeabilizing Gram-negative bacteria. The permeabilization of Gram-positive bacteria requires additional measures, e.g. using components such as organic solvents, for example toluene, xylene, acetone, ethanol, etc., detergents, for example SDS, Nonidet, etc., and cell wall-decomposing enzymes, for example lysozyme, lysostaphin, mutanolysin, etc.

The hybridization reaction is carried out in two steps, i.e. (a) incubation of the permeabilized sample with the labeled probe or the probe mixture, and (b) a subsequent washing step for removing non-specifically bound probes, with this being followed by the evaluation. The probes (1–1000 ng) are incubated in an aqueous solution for several hours at a temperature which can be derived from the formula for calculating the dissociation temperature of RNA/DNA hybrids (Lathe, 1985; Wahl et al., 1987): $Td=81.5+16.6 \lg[Na^+]=0.4$ (% GC)$-820/n-0.5$ (% FA); n=length of the oligonucleotide; FA=formamide. The essential components of the aqueous solution are chaotropic substances, such as salts and/or formamide, which ensure specific binding of the probes to the complementary target sequences on rRNA, and a detergent for suppressing nonspecific binding of the probes, e.g. to proteins. In principle, the solution for washing out the nonspecifically bound probes has a similar composition, with the constituents which affect the binding of the probes being employed in lower concentrations and/or the temperature being correspondingly increased. Finally, the excess washing buffer is removed from the microscope slides with a buffered salt solution, e.g. PBS, and the sample region is embedded in Citifluor AF1 (Citifluor Ltd., London, UK) in order to decrease fading of the fluorescent probes during the investigation. The result of the detection reaction is read off using a fluorescence microscope (standard filter for red and green fluorescence and/or a combined filter for simultaneously detecting red and green fluorescence).

Example 8

It has been observed that, under unfavorable living conditions, *H. pylori* changes its morphology and converts itself from the known rod form into a coccoid form. It is known that this coccoid form can no longer be cultured and is consequently not accessible to classical microbiological investigations. If these forms are indeed survival stages of *H. pylori*, it has to be possible to diagnose them.

A series of experiments was carried out in order to examine to what extent the coccoid forms are available for the above-described detection process for determining antibiotic resistance. A clarithromycin-resistant *H. pylori* strain was converted into its coccoid form by storing it in distilled water for one week at 4° C. After this period of time, all the rod-shaped *H. pylori* cells had been completely transformed into coccoid forms, which no longer grew on conventional culture media. These coccoid cells were subjected to the above-described detection process using the known probe mixture. Success was in fact achieved in identifying the coccoid form as being *H. pylori* and, something which is particularly important, clarithromycin-resistance was detected as well. Since then, the above-described process has even been used to successfully detect these forms in human tissue biopsies.

This is, therefore, the first detection method which is available for determining resistance to an antibiotic in coccoid *Helicobacter*. In addition to this, it was not to be expected that this method would function in coccoid *H. pylori*. There have been many reports in the literature that the coccoid form has a greatly reduced content of rRNA and that, furthermore, this rRNA is degraded (Donelli et al., 1998; Narikawa et al., 1997). Our investigations prove that the coccoid form which is induced in $H_2O$ has a content of rRNA which is sufficient to be detected, and can be very readily characterized by an in-situ hybridization which is directed toward the rRNA.

Investigating coccoid forms assumes greater significance particularly in connection with determining resistance. It is known that coccoid forms preferentially arise in association with sublethal antibiotic concentrations and that these forms are therefore possibly connected with failures in antibiotic therapy. In addition to this, it is probable that these forms occur at high concentrations in the stools of infected patients and that the above-described process can therefore be used to detect an acute *H. pylori* infection with a clarithromycin-resistant organism simply and rapidly, i.e. without the gastroendoscopic removal of a biopsy sample.

REFERENCE LIST

Amann, R. I., L. Krumholz and D. Stahl. 1990. Fluorescent oligonucleotide probing of whole cells for determinative, phylogenetic and environmental studies in microbiology. J. Bacteriol. 172:762–770.

Beimfohr, C., A. Krause, R. Amann, W. Ludwig and K.-H. Schleifer. 1993. In situ identification of Lactococci, Enterococci and Streptococci. System. Appl. Microbiol. 16:450–456.

Berry, V., K. Jennings and G. Woodnutt (1995) Bactericidal and morphological effects of amoxicillin on *Helicobacter pylori*. Antimicrob Agents Chemother 39: 1859–1861.

Bizzozero, G. (1893) Ueber die schlauchformigen drusen des magendarmkanals und die bezeihungen ihres epithets zu dem oberflachenepithel der schleimhaut (On the tubular glands of the gastrointestinal tract and the relationships of their epithelium to the surface epithelium of the mucous membrane). *Arch Mikr Anast* 42: 82

Bode, G., F. Mauch and P. Malfertheiner. (1993) The coccoid forms of *Helicobacter pylori*. Criteria for their viability. Epidemiol Infect 111: 483–490.

Brimacombe, R. B., B. Greuer, P. Mitchell, M. Osswald, J. Rinke-Appel, D. Schuler, and K. Stade. 1990. Three dimensional structure and function of *E. coli* 16S and 23S rRNA as studied by crosslinking techniques, p. 93–106. In E. Hill, A. Dahlberg, R. A. Garrett, P. B. Moore, D. Schlessinger, and J. R. Warner (ed.) The ribosome, structure function, and evolution. American Society of Microbiology, Washington, D.C.

Brosius, J., T. J. Dull, D. D. Sleeter and H. F. Noller. 1981. Gene organization and primary structure of a ribosomal RNA operon from *Escherichia coli*. J. Mol. Biol. 148: 107–127.

Buckley, M. J., Xia, H. X., Hyde, D. M., Keane, C. T. and O'Morain, C. A. (1997) Metronidazole resistance reduces efficacy of triple therapy and leads to secondary clarithromycin resistance. *Dig Dis Sci* 42: 2111–2115.

Cao, J., Z. Q Li, K. Borch, F. Petersson and S. Mardh. (1997) Detection of spiral and coccoid forms of *Helicobacter pylori* using a murine monoclonal antibody. Clin Chim Acta 267: 183–196.

Cellini, L., N. Allocati, D. Angelucci, T. Iezzi, E. Di Campli, L. Marzio and B. Dainelli. (1994) Coccoid *Helicobacter pylori* not culturable in vitro reverts in mice. Microbiol Immunol 38: 843–850.

Chan, W. Y., P. K. Hui, K. M. Leung, J. Chow, F. Kwok and C. S. Ng. (1994) Coccoid forms of *Helicobacter pylori* in the human stomach. Am J Clin Pathol 102: 503–507.

DeLong, E. F., G. S. Wickham, and N. R. Pace. 1989. Phylogenetic stains: ribosomal RNA-based probes for the identification of single microbial cells. Science. 243: 1360–1363.

Dent J. C., C. A. M. McNulty, J. C. Uff, S. P. Wilkinson, and M. W. L. Gear. 1987. Spiral organism in the gastric antrum, Lancet ii:96.

Desroches, J. J., Lahaie, R. G., Picard, M., Morais, J., Dumont, A., Gaudreau, C., Picard, D., Chartrand, R., Methodological validation and clinical usefulness of carbo-14-urea breath test for documentation of presence and eradication of *Helicobacter pylori* infection. J. Nucl. Med. 1997 38(7) 1141–1145.

Donelli, G., P. Matarrese, C. Fiorentini, B. Dainelli, T. Taraborelli, E. Di Campli, S. Di Bartolomeo and L. Cellini. (1998) The effect of oxygen on the growth and cell morphology of *Helicobacter pylori*. FEMS Microbiol Lett 168: 9–15.

Eaton, K. A., C. E. Catrenich, K. M. Makin, and S. Krakowka. (1995) Virulence of coccoid and bacillary forms of *Helicobacter pylori* in gnotobiotic piglets. JID 171: 459–462.

Forman, D., Coleman, M., Debacker, G., Eider, J., Moller, H., Damotta, L. C., Roy, P., Abid, L., Tjonneland, A., Boeing, H., Haubrich, T., Wahrendorf, J., Manousos, O., Tulinius, H., Ogmundsdottir, H., Palli, D., Cipriani, F., Fukao, A., Tsugane, S., Miyajima, Y. et al. (1993) An international association between *Helicobacter pylori* infection and gastric cancer. Lancet 341: 1359–1362.

Forsgren J., A. Samuelson, A. Ahlin, J. Jonasson, B. Rynnel-Dagöö, and Alf Lindberg. *Haemophilus influenzae* resides and multiplies intracellularly in human adenoid tissue as demonstrated by in situ hybridization and bacterial viability assay. Infect. Immun. 1994. 62:673–679.

Frischer, M. E. Floriania P. J., and Nierzwicki-Bauer, 1996. Differential sensitivity of 16S rRNA targeted oligonucleotide probes . . . Can. J. Microbiol. 42:1061–1071.

Giovannoni, S. J., E. F. De Long, G. J. Olsen, and N. R. Pace. 1988. Phylogenetic group-specific oligonucleotide probes for identification of single microbial cells. J. Bacteriol. 170:720–726.

Goodwin, C. S., Armstrong, J. A., Chilvers, T., Peters, M., Collins, M. D., Sly, L., McConnell, W. and Harper, W. E. S. (1989) Transfer of *Campylobacter pylori* and *Campylobacter mustelae* to Helicobacter gen. nov. as *Helicobacter pylori* comb. nov. and *Helicobacter mustelae* comb. nov., respectively. Int J Syst Bact 39:397–405.

Graham, D. Y. (1995) clarithromycin for treatment of *Helicobacter pylori* infections. *Eur J Gastroenterol Hepatol* 7 Suppl 1: pp. 55–8.

Hentschel, E., Nemec, H., Schultze, K., Hirschl, A., Dragosics, B., Brandstatter, G and Taufer, M. (1991) Duodenal ulcer recurrence and *Helicobacter pylori* [letter; comment]. *Lancet* 338: 569.

Holck, S., et al., 1997. APMIS 105; 746–756.

Isaacson, P. G. and Spencer, J. (1993) Is gastric lymphopma an infectious disease? *Hum Pathol* 24: 569–570.

Jablonowski, H., Fatkenheuer, G., Youle, M., Newell, T., Lines, S. and Craft, J. C. (1997) Ancillary benefits of *Mycobacterium avium-intracellulare* complex prophylaxis with clarithromycin in HIV-infected patients. *Drugs* 54 Suppl 2: 16–22.

Khin, M. M., M. Ringner, P. Aleljung, T. Wadström and B. Ho. (1996) Binding of human plasminogen and lactoferrin by *Helicobacter pylori* coccoid forms. J Med Microbiol 45: 433–439.

Kusters, J. G., M. M. Gerrits, J. A. Van Strijp and C. M. Vandenbroucke-Grauls. (1997) Coccoid forms of *Helicobacter pylori* are the morphologic manifestation of cell death. Infect Immun 65: 3672–3679.

Langendijk, P. S., F. Schut, G. J. Jansen, G. C. Raangs, G. R. Kamphuis, M. H. F. Wilkinson, and G. W. Welling. 1995. Quantitative fluorescence in situ hybridization of *Bifidobacterium* spp. with genus-specific 16S rRNA-targeted probes and its application in fecal samples. Appl. Environ. Microbiol. 61: 3069–3075.

Lathe, R. (1985) Synthetic oligonucleotide probes deduced from amino acid sequence data. Theoretical and practical considerations. J. Mol. Biol, 183: 1–12.

Lischewski A., R. I. Amann, D. Harmsen, H. Merkert, J. Hacker, and J. Morschhäuser. 1996. Specific detection of *Candida albicans* and *Candida tropicalis* by fluorescent in situ hybridization with an 18S rRNA-targeted oligonucleotide probe. Microbiology. 142: 2731–2740.

Lischewski A., M. Kretschmar, H. Hof, R. Amann, J. Hacker, and J. Morschhäuser. 1997. Detection and Identification of *Candida* Species in experimentally infected tissue and human blood by rRNA-specific fluorescent in situ hybridization. J. Clin. Microbiol. 35: 2943–2948.

Lucier, T. S., K. Heitzman, S.-K. Liu, and P.-C. Hu. 1995. Transition mutation in the 23S rRNA of Erythromycin-resistent isolates of *Mycoplasma pneumoniae*. Antimicrob. Agents Chemother. 39: 2770–2773.

Malfertheiner, P. (1994) *Helicobacter pylori—Von der Grundlage zur Therapie* (*Helicobacter* pylori—from basic principles to therapy). Georg Thieme Verlag, Stuttgart, N.Y.

Marshall, B. J., Royce, H., Annear, D. I. Goodwin, C. S., Pearman, J. W., Warren, J. R. and Armstrong, J. A. (1984) Original isolation of *Campylobacter pyloridis* from human gastric mucosa. *Microbios Lett* 25: 83–88.

Meier, A., P. Kirschner, B. Springer, V. A. Steingrube, B. A. Brown, R. J. Wallace, and E. Boettger. 1994. Identification of mutations in the 23S ribosomal RNA gene of clarithromycin resistant *Mycobacterium intracellulare*. Antimicrob. Agents Chemother. 38:381–384.

Morotomi, M., Hoshina, S., Green, P. et al., 1989, J. Clin. Microbiol. 27(12):2652–2655.

Narikawa, S., S. Kawai, H. Aoshima, O. Kawamata, R. Kawaguchi, K. Hikiji, M. Kato, S. Iino and Y. Mizushima. (1997) Comparison of the nucleic acids of helical and coccoid forms of *Helicobacter pylori*. Clin Diagn Lab Immunol 4: 285–290.

Neefs J-M., Y. Van de Peer, P. De Rijk, S. Chapelle, and R. De Wachter, 1993. Compilation of small ribosomal subunit RNA structure. Nuc. Acids Res. 21:3025–3049.

Noller, H. F., V. Hoffarth, and L. Zimniak. 1992. Unusual resistance of peptidyl transferase to protein extractzion [sic] procedures. Science. 256:1416–1419.

Nordentoft, S., H. Christensen, and H. C. Wegner. 1997. Evaluation of a fluorescence-labelled Oligonucleotide probe targeting 23S rRNA for in situ detection of *Salmonella* Serovars in Paraffin-Embedded tissue sections and their rapid identification in bacterial smears. J. Clin. Microbiol. 35: 2642–2648.

Palu, G., S. Valisena, M. F. Barile, and G. A. Meloni. 1989. Mechanism of Macrolide resistance in *Ureaplasma urealyticum*: a study on collection and clinical strains. Eur. J. Epidemiol. 5:146–153.

Ramsing, N. B., M. Kühl, and B. B. Jorgensen. 1993. Distribution of sulfate-reducing bacteria, $O_2$, and $H_2S$ in photosynthetic biofilms determined by oligonucleotide probes and microelectrodes. Appl. Environ. Microbiol. 59: 3840–3849.

Ross et al. 1997. Clinical resistance to erythromycin and clindamycin in cutaneous propionibacteria isolated from acne patients is associated with mutations in 23S rRNA. Antimicrob. Agents Chemother. 41: 1162–1165.

Sambrook, J., E. F. Fritsch, T. Maniatis. (1989) Molecular cloning: a laboratory manual. Cold Spring Harbor Laboratory Press, Cold Spring Harbor, N.Y.

Schaechter, O., O. Maaloe, and N. O. Kjeldgaard. 1958. Dependence on medium and temperature of cell size and chemical composition durin [sic] balanced growth of *Salmonella typhimurium*. J. Gen. Microbiol. 19:592–606.

Schwarz, E., Plum, G., Hasbach, H., Eidt, S., Schrappe, M., Kruis, W.: Molecular biology in diagnosis and epidemiology of *Helicobacter pylori*: PCR for the detection and AP-PCR for characterization of patient isolates. Zentrbl. Bakteriol. 1997, 285(3), 368–378.

Segal, E. D., S. Falkow and L. S. Tompkins. (1996) *Helicobacter pylori* attachment to gastric cells induces cytoskeletal rearrangements and tyrosine phosphorylation of host cell proteins. Proc Natl Acad Sci USA 93: 1259–1264.

Sigmiund, C. D., M. Ettayebi, and E. A. Morgan. 1988. Antibiotic resistance mutations in ribosomal RNA genes of *Escherichia coli*. Methods Enzymol. 164:673–690.

Sipponen, P. and Hyvärinen, H. (1993) Role of *Helicobacter pylori* in the pathogenesis of gastritis, peptic ulcer and gastric cancer. *Scand J Gastroenterol* 28: 3–6.

Solnick, J. V., J. O'Rourke, A. Lee, B. J. Paster, F. E. Dewhirst, and L. S. Tompkin. 1993. An uncultured gastric spiral organism is a newly identified *Helicobacter* in humans. J. Infect. Dis. 168:379–385.

Sorberg, M., M. Nilsson, H. Hanberger and L. E. Nilsson. (1996) Morphologic conversion of *Helicobacter pylori* from bacillary to coccoid form. Eur J Clin Microbiol Infect Dis 15:216–219.

Stolte, M. and Eidt, S. (1993) Healing gastric MALT lymphomas by eradicating *H. pylori*. Lancet 342: 568

Stopler, T. and D. Branski. 1986. Resistance of *Mycoplasma pneumoniae* to macrolides, lincomycin, and streptograminB. J. Antimicrob. Chemother. 18:359–364.

Taylor, D. N. and Blaser, M. J. (1991) The epidemiology of *Helicobacter pylori* infection. *Epidemiol Rev* 13: 42–59.

Trebesius K., D. Harmsen, A. Rakin, J. Schmelz and J. Heesemann. 1998. Development of rRNA targeted PCR and in situ hybridization with fluorescently labelled oligonucleotides for detection of *Yersinia* species. J. Clin. Microbiol, 36, in press.

Vester, B., and R. A. Garrett. 1987. A plasmid-coded and site-directed mutation in *Escherichia coli* 23S rRNA that confers resistance to erythromycin: implications for the mechanism of action of erythromycin. Biochimie 69:891–900.

Versalovic, J., M. S. Osato, K. Spakovsky, M. P. Dore, R. Reddy, G. G. Stone, D. Shortridge, R. K. Flamm, S. K. Tanaka and D. Y. Graham. 1997. Point mutations in the 23S rRNA gene of *Helicobacter pylori* associated with different levels of clarithromycin resistance. J. Antimicrob, Chemotherapy. 40: 283–286.

Wagner, M., R. Amann, H. Lemmer, and K. H. Schleifer. 1993. Probing activated sludge with proteobacteria-specific oligonucleotides: inadequacy of culture-dependent methods for describing microbial community structure. Appl. Environ. Microbiol. 59:1520–1525.

Wagner, M., G. Rath, R. Amann, H.-P. Koops, and K. H. Schleifer. 1995. In situ identification of ammonia-oxidizing bacteria. System. Appl. Microbiol. 18: 251–264.

Wahl, G. M., S. L. Berger and A. R. Kimmel. (1987) Molecular hybridization of immobilized nucleic acids; theoretical concepts and practical considerations. Methods in Enzymology 152:339–407.

Wang, X., E. Sturegard, R. Rupar, H. O. Nilsson, P. A. Aleljung, B. Carlen, R. Willen and T. Wadström. (1997) Infection of BALB/c A mice by spiral and coccoid forms of *Helibacter pylori*. J Med Microbiol 46: 657–663.

Warren, J. R. and Marshall, B. (1983) Unidentified curved bacilli on gastric epithelium in active chronic gastritis. *Lancet* i: 1273–1275

Weisblum, B. 1995. Erythromycin resistance by ribosome modification. Antimicrob. Agents Chemother. 39:577–585.

Westblom, T. U., E. Madan, and B. R. Midkiff. 1991. Egg yolk emulsion agar, a new medium for the cultivation of *Helicobacter pylori*. Journal of Clinical Microbiology 29: 819–821.

Woese, C. R. 1987. Bacterial evolution. Microbiol, Rev. 51:221–271.

Zuckerkandl, E., and L. Pauling. 1965. Molecules as documents of evolutional history. J. Theoret. Biol. 8:357–366.

The invention claimed is:

1. A process for detecting macrolide antibiotic resistance in microorganisms, comprising the steps of:
    a) preparing a sample containing microorganisms suspected of being resistant to macrolide antibiotics,
    b) contacting the sample with a mixture of hybridization probes specific for a region of the peptidyltransferase center from a 23S rRNA, in situ, wherein said mixture of hybridization probes specifically detect a point mutation at a nucleotide which corresponds to one or more of the nucleotides 2032, 2057, 2058, 2059 and 2611 on the *E. coli* 23S rRNA, under conditions which permit the probes to hybridize specifically, and said mixture of hybridization probes further comprises a hybridization probe specific for a wild type nucleic acid sequence, and
    c) analyzing the sample by determining the appearance of in situ hybridization between said hybridization probes and nucleic acids in said sample as an indication of macrolide antibiotic resistance, wherein the microorganisms are not cultured prior to contact with said hybridization probe and wherein said hybridization probe specific for a wild type nucleic acid sequence is unlabeled and said hybridization probes which specifically detect a point mutation at a nucleotide which corresponds to one or more of the nucleotides 2032, 2057, 2058, 2059 and 2611 on the *E. coli* 23S rRNA are labeled.

2. The process according to claim 1, wherein said nucleic acids in said sample contain a sequence selected from the group consisting of SEQ ID NO:1, SEQ ID NO:2 and SEQ ID NO:3.

3. The process according to claim 1, wherein said wild type nucleic acid sequence includes the sequence according to SEQ ID NO:4.

4. The process according to claim 1, wherein said microorganisms are slowly growing pathogens and/or pathogens which are difficult to culture, or cannot be cultured in vitro.

5. The process according to claim 4, wherein said microorganisms are selected from the group consisting of *Helicobacter, mycobacteria, Porphyromonas gingivalis, Propionibacterium acnes, Borrelia burgdorferi*, mycoplasmas, chlamydias, *Tropheryma whippelii*, bartonellas, legionellas, nocardias and actinomycetes.

6. The process according to claim 1, wherein said sample is derived from human or animal tissues or body fluids.

7. The process according to claim 1, wherein the sample is subjected to a procedure for enriching microorganisms.

8. The process according to claim 1, wherein a presumptive medium is added to the sample prior to step a).

9. The process according to claim 8, wherein said presumptive medium contains an indicator substance for typing microorganisms.

10. The process according to claim 1, wherein the sample is fixed.

11. The process according to claim 10, wherein said sample is permeabilized.

12. The process according to claim 1, wherein the hybridization probe is selected from the group consisting of nucleic acids and nucleic acid analogues.

13. The process according to claim 12, wherein said nucleic acid analogues are PNA.

14. The process according to claim 12, wherein said nucleic acids are DNA.

15. The process according to claim 1, wherein the hybridization probe includes a hybridization region having a length of 10 to 30 nucleotides.

16. The process according to claim 15, wherein said hybridization probe has a length of 15 to 20 nucleotides.

17. The process according to claim 16, wherein said hybridization probe has a length of 17 to 18 nucleotides.

18. The process according to claim 1, wherein said hybridization probe is specific for mutations selected from deletions, transversions, transitions and modifications of the wild type sequence.

19. The process according to claim 1, wherein several hybridization probes are used which are specific for different nucleic acid sequences associated with antibiotic resistance.

20. The process according to claim 1, wherein said hybridization probe is selected from the group consisting of ClaR1 (SEQ ID NO: 1), ClaR2 (SEQ ID NO:2) and ClaR3 (SEQ ID NO:3).

21. The process according to claim 1, further comprising at least one hybridization probe specific for a species or a genus of said microorganism.

22. The process according to claim 1, said hybridization probe which specifically detects a point mutation carries a direct label.

23. The process according to claim 1, wherein said hybridization probes which specifically detects a point mutation are labeled, or can be labeled, with dye groups, fluorescence groups and/or enzyme groups.

24. The process according to claim 1, wherein more than one hybridization probe which specifically detects a point mutation is used and said probes which specifically detect a point mutation are labeled or can be labeled differently.

25. The process according to claim 1, wherein the sample is analyzed in step c) by microscopic methods.

26. The process according to claim 1, wherein the analysis in step c) comprises quantitatively determining antibiotic resistance.

27. The process according to claim 1, wherein said microorganism is a *Helicobacter* and said nucleic acid sequence comprises SEQ ID NO.1.

* * * * *

SEQUENCE LISTING

<160> NUMBER OF SEQ ID NOS: 12

<210> SEQ ID NO 1
<211> LENGTH: 17
<212> TYPE: DNA
<213> ORGANISM: helicobacter pylori A2058G (ClaR)

<400> SEQUENCE: 1
cggggtcttc ccgtctt                                               17

<210> SEQ ID NO 2
<211> LENGTH: 17
<212> TYPE: DNA
<213> ORGANISM: helicobacter pylori A2059G

<400> SEQUENCE: 2
cggggtctct ccgtctt                                               17

<210> SEQ ID NO 3
<211> LENGTH: 17
<212> TYPE: DNA
<213> ORGANISM: helicobacter pylori A2058C (ClaR)

<400> SEQUENCE: 3
cggggtcttg ccgtctt                                               17

<210> SEQ ID NO 4
<211> LENGTH: 17
<212> TYPE: DNA
<213> ORGANISM: helicobacter pylori wild type

<400> SEQUENCE: 4
cggggtcttt ccgtctt                                               17

<210> SEQ ID NO 5
<211> LENGTH: 18
<212> TYPE: DNA
<213> ORGANISM: helicobacter pylori

<400> SEQUENCE: 5
gctttcgcgc aatcagcg                                              18

<210> SEQ ID NO 6
<211> LENGTH: 18
<212> TYPE: DNA
<213> ORGANISM: helicobacter pylori

<400> SEQUENCE: 6
aggcacatga tctatgcg                                              18

<210> SEQ ID NO 7
<211> LENGTH: 21
<212> TYPE: DNA
<213> ORGANISM: helicobacter pylori

<400> SEQUENCE: 7
cacacctgac tgactatccc g                                          21

<210> SEQ ID NO 8
<211> LENGTH: 22
<212> TYPE: DNA
<213> ORGANISM: helicobacter pylori

```
<400> SEQUENCE: 8
ggacataggc tgatctctta gc                                              22

<210> SEQ ID NO 9
<211> LENGTH: 20
<212> TYPE: DNA
<213> ORGANISM: helicobacter heilmannii

<400> SEQUENCE: 9
cccacactcc agaagratag                                                 20

<210> SEQ ID NO 10
<211> LENGTH: 21
<212> TYPE: DNA
<213> ORGANISM: helicobacter heilmannii

<400> SEQUENCE: 10
cccacactct agggttkgca g                                               21

<210> SEQ ID NO 11
<211> LENGTH: 20
<212> TYPE: DNA
<213> ORGANISM: helicobacter heilmannii

<400> SEQUENCE: 11
cccacactct agaaagatag                                                 20

<210> SEQ ID NO 12
<211> LENGTH: 21
<212> TYPE: DNA
<213> ORGANISM: helicobacter heilmannii

<400> SEQUENCE: 12
cacatctgac ttgccacccc g                                               21
```